(12) United States Patent
Miller et al.

(10) Patent No.: US 7,314,926 B1
(45) Date of Patent: Jan. 1, 2008

(54) ANTIPROLIFERATIVE ACTIVITY OF G-RICH OLIGONUCLEOTIDES AND METHOD OF USING SAME TO BIND TO NUCLEOLIN

(75) Inventors: Donald M. Miller, Louisville, KY (US); Paula J. Bates, Louisville, KY (US); John O. Trent, Louisville, KY (US)

(73) Assignee: Antisoma Research Limited, London (GB)

( * ) Notice: Subject to any disclaimer, the term of this patent is extended or adjusted under 35 U.S.C. 154(b) by 0 days.

(21) Appl. No.: 09/958,251

(22) PCT Filed: Apr. 7, 2000

(86) PCT No.: PCT/US00/09311

§ 371 (c)(1),
(2), (4) Date: Feb. 27, 2002

(87) PCT Pub. No.: WO00/61597

PCT Pub. Date: Oct. 19, 2000

Related U.S. Application Data

(60) Provisional application No. 60/128,316, filed on Apr. 8, 1999, provisional application No. 60/149,823, filed on Aug. 19, 1999.

(51) Int. Cl.
*C07H 21/04* (2006.01)
*A61K 48/00* (2006.01)

(52) U.S. Cl. .................. 536/24.1; 536/23.1; 514/44

(58) Field of Classification Search .................. None
See application file for complete search history.

(56) References Cited

U.S. PATENT DOCUMENTS

| | | |
|---|---|---|
| 5,176,996 A | 1/1993 | Hogan et al. |
| 5,262,409 A | 11/1993 | Margolis et al. |
| 5,310,892 A | 5/1994 | Aris et al. |
| 5,342,774 A | 8/1994 | Boon et al. |
| 5,359,047 A | 10/1994 | Donahue et al. |
| 5,416,202 A | 5/1995 | Bernhard et al. |
| 5,432,070 A | 7/1995 | Schumacher et al. |
| 5,443,962 A | 8/1995 | Draetta et al. |
| 5,444,149 A | 8/1995 | Keene et al. |
| 5,449,758 A | 9/1995 | Hartley |
| 5,470,971 A | 11/1995 | Kondo et al. |
| 5,489,508 A | 2/1996 | West et al. |
| 5,494,818 A | 2/1996 | Baker et al. |
| 5,495,070 A | 2/1996 | John |
| 5,523,389 A | 6/1996 | Ecker et al. |
| 5,561,222 A | 10/1996 | Keene et al. |
| 5,582,981 A | 12/1996 | Toole et al. |
| 5,583,016 A | 12/1996 | Villeponteau et al. |
| 5,594,120 A | 1/1997 | Brenner et al. |
| 5,612,201 A | 3/1997 | De Plaen et al. |
| 5,614,503 A | 3/1997 | Chaudhary et al. |
| 5,624,799 A | 4/1997 | Kohwi-Shigematsu et al. |
| 5,624,818 A | 4/1997 | Eisemann et al. |
| 5,625,031 A | 4/1997 | Webster et al. |
| 5,631,146 A | 5/1997 | Szostak et al. |
| 5,643,778 A | 7/1997 | Nishikura |
| 5,643,890 A | 7/1997 | Iversen et al. |
| 5,645,986 A | 7/1997 | West et al. |
| 5,656,430 A | 8/1997 | Chirikjian et al. |
| 5,670,621 A | 9/1997 | Donahue et al. |
| 5,677,428 A | 10/1997 | Nishikura |
| 5,686,306 A | 11/1997 | West et al. |
| 5,688,511 A | 11/1997 | Gaynor et al. |
| 5,691,145 A | 11/1997 | Pitner et al. |
| 5,695,932 A | 12/1997 | West et al. |
| 5,705,334 A | 1/1998 | Lippard et al. |
| 5,707,795 A | 1/1998 | West et al. |
| 5,714,575 A | 2/1998 | Inouye et al. |
| 5,734,040 A | 3/1998 | Weeks et al. |
| 5,741,677 A | 4/1998 | Kozlowski et al. |
| 5,756,710 A | 5/1998 | Stein et al. |
| 5,763,174 A | 6/1998 | Nishikura |
| 5,763,178 A | 6/1998 | Chirikjian et al. |
| 5,776,696 A | 7/1998 | Salowe |
| 5,780,447 A | 7/1998 | Nienhuis |
| 5,780,610 A | 7/1998 | Collins et al. |
| 5,783,398 A | 7/1998 | Marcy et al. |
| 5,792,613 A | 8/1998 | Schmidt et al. |
| 5,804,380 A | 9/1998 | Harley et al. |
| 5,834,247 A | 11/1998 | Comb et al. |
| 5,837,453 A | 11/1998 | Harley et al. |
| 5,837,857 A | 11/1998 | Villeponteau et al. |
| 5,843,732 A | 12/1998 | Davis et al. |

(Continued)

FOREIGN PATENT DOCUMENTS

WO     WO 99/07383     2/1999

(Continued)

OTHER PUBLICATIONS

Burgess et al. The antiproliferative activity of c-myb and c-myc antisense oligonucleotides in smooth muscle cells is caused by a nonantisense mechanism. Proc Natl Acad Sci U S A. Apr. 25, 1995;92(9):4051-5.*

(Continued)

*Primary Examiner*—Daniel M. Sullivan
(74) *Attorney, Agent, or Firm*—Morgan Lewis & Bockius LLP

(57) ABSTRACT

The present invention provides a method for inhibiting the proliferation of malignant and/or hyperplastic cells in a subject by administering to the subject a therapeutically effective amount of a guanosine rich oligonucleotide. The present invention also provides oligonucleotides which are capable of being specifically bound to a specific cellular protein which is nucleolin and/or nucleolin-like in nature, which is implicated in the proliferation of cells, specifically malignant and/or hyperplastic cells, and a method for their selection.

8 Claims, 14 Drawing Sheets

U.S. PATENT DOCUMENTS

| | | |
|---|---|---|
| 5,849,564 A | 12/1998 | Chang et al. |
| 5,854,223 A | 12/1998 | Stein et al. |
| 5,861,498 A | 1/1999 | Alnemri et al. |
| 5,863,726 A | 1/1999 | Harley et al. |
| 5,866,680 A | 2/1999 | Keene et al. |
| 5,888,739 A | 3/1999 | Pitner et al. |
| 5,891,639 A | 4/1999 | Harley et al. |
| 5,925,729 A | 7/1999 | Boon et al. |
| 5,932,475 A | 8/1999 | Bandman et al. |
| 5,932,556 A | 8/1999 | Tam |
| 5,948,680 A | 9/1999 | Baker et al. |
| 5,952,490 A | 9/1999 | Hanecak et al. |
| 5,968,506 A | 10/1999 | Weinrich et al. |
| 5,972,692 A | 10/1999 | Hashimoto et al. |
| 5,985,320 A | 11/1999 | Edwards et al. |
| 5,989,823 A | 11/1999 | Jayasena et al. |
| 5,989,860 A | 11/1999 | Bandman et al. |
| 5,994,072 A | 11/1999 | Lam et al. |
| 6,013,639 A | 1/2000 | Peyman et al. |
| 6,017,536 A | 1/2000 | Barney et al. |
| 6,017,709 A | 1/2000 | Hardin et al. |
| 6,020,139 A | 2/2000 | Schwartz et al. |
| 6,025,194 A | 2/2000 | Funk |
| 6,025,474 A | 2/2000 | Van den Eynde et al. |
| 6,027,881 A | 2/2000 | Paviakis et al. |
| 6,028,058 A | 2/2000 | Florkiewicz |
| 6,030,955 A | 2/2000 | Stein et al. |
| 6,036,955 A | 3/2000 | Thorpe et al. |
| 6,037,329 A | 3/2000 | Baird et al. |
| 6,054,265 A | 4/2000 | Barney et al. |
| 6,054,442 A | 4/2000 | Chen et al. |
| 6,057,423 A | 5/2000 | Brenner et al. |
| 6,060,065 A | 5/2000 | Barney et al. |
| 6,063,906 A | 5/2000 | Brenner et al. |
| 6,068,973 A | 5/2000 | Barney et al. |
| 6,071,732 A | 6/2000 | Moore |
| 6,080,727 A | 6/2000 | Zupi |
| 6,093,399 A | 7/2000 | Thorpe et al. |
| 6,093,794 A | 7/2000 | Barney et al. |
| 6,107,029 A | 8/2000 | Giordano |
| 6,121,434 A | 9/2000 | Peyman et al. |
| 6,126,965 A | 10/2000 | Kasid et al. |
| 6,127,173 A | 10/2000 | Eckstein et al. |
| 6,127,175 A | 10/2000 | Vigne et al. |
| 6,153,408 A | 11/2000 | Abastado et al. |
| 6,165,786 A | 12/2000 | Bennett et al. |
| 6,165,789 A | 12/2000 | Monia et al. |
| 6,166,178 A | 12/2000 | Cech et al. |
| 6,171,843 B1 | 1/2001 | Bandman et al. |
| 6,177,254 B1 | 1/2001 | Rattner et al. |
| 6,180,348 B1 | 1/2001 | Li |
| 6,183,751 B1 | 2/2001 | Chang et al. |
| 6,194,206 B1 | 2/2001 | West et al. |
| 6,200,746 B1 | 3/2001 | Fisher et al. |
| 6,214,805 B1 | 4/2001 | Torrence et al. |
| 6,228,983 B1 | 5/2001 | Barney et al. |
| 6,235,313 B1 | 5/2001 | Mathiowitz et al. |
| 6,235,525 B1 | 5/2001 | van den Eynde et al. |
| 6,251,585 B1 | 6/2001 | Draetta et al. |
| 6,255,055 B1 | 7/2001 | Ross |
| 6,261,556 B1 | 7/2001 | Weinrich et al. |
| 6,265,548 B1 | 7/2001 | Paviakis et al. |
| 6,274,313 B1 | 8/2001 | Weeks et al. |
| 6,274,725 B1 | 8/2001 | Sanghvi et al. |
| 6,288,042 B1 | 9/2001 | Rando et al. |
| 6,291,187 B1 | 9/2001 | Kingsmore et al. |
| 6,300,321 B1 | 10/2001 | Scherman et al. |
| 6,313,266 B1 | 11/2001 | Bandman et al. |
| 6,316,200 B1 | 11/2001 | Nadeau et al. |
| 6,320,039 B1 | 11/2001 | Villeponteau et al. |
| 6,323,185 B1 | 11/2001 | Rando et al. |
| 6,331,396 B1 | 12/2001 | Silverman et al. |
| 6,331,617 B1 | 12/2001 | Weeks et al. |
| 6,332,897 B1 | 12/2001 | Weiner et al. |
| 6,333,191 B1 | 12/2001 | Inouye et al. |
| 6,333,314 B1 | 12/2001 | Kasid et al. |
| 6,335,170 B1 | 1/2002 | Orntoft |
| 6,348,586 B1 | 2/2002 | Chang et al. |
| 6,355,785 B1 | 3/2002 | Rando et al. |
| 6,365,187 B2 | 4/2002 | Mathiowitz et al. |
| 6,368,789 B1 | 4/2002 | West et al. |
| 6,376,226 B1 | 4/2002 | Alnermri |
| 6,379,888 B1 | 4/2002 | Nadeau et al. |
| 6,383,752 B1 | 5/2002 | Agrawal et al. |
| 6,399,302 B1 | 6/2002 | Lannigan et al. |
| 6,399,392 B1 | 6/2002 | Haugland et al. |
| 6,416,959 B1 | 7/2002 | Giuliani et al. |
| 6,420,122 B1 | 7/2002 | Housman et al. |
| 6,423,493 B1 | 7/2002 | Gorenstein et al. |
| 6,426,231 B1 | 7/2002 | Bayley et al. |
| 6,444,643 B1 | 9/2002 | Steiner et al. |
| 6,444,870 B1 | 9/2002 | Zhang et al. |
| 6,455,042 B1 | 9/2002 | Brenner et al. |
| 6,455,250 B1 | 9/2002 | Aguilera et al. |
| 6,465,176 B1 | 10/2002 | Giordano et al. |
| 6,475,789 B1 | 11/2002 | Cech et al. |
| 6,475,791 B1 | 11/2002 | Lippard et al. |
| 6,479,055 B1 | 11/2002 | Bolognesi et al. |
| 6,479,301 B1 | 11/2002 | Balch et al. |
| 2001/0041681 A1 | 11/2001 | Phillips et al. |

FOREIGN PATENT DOCUMENTS

| | | |
|---|---|---|
| WO | WO 99/42113 | 8/1999 |
| WO | WO 01/44465 | 6/2001 |

OTHER PUBLICATIONS

Dermer G. Another Anniversary for the war on cancer, 1994, Bio/Technol. 12:320.*

Zendegui et al. In vivo stability and kinetics of absorption and disposition of 3' phosphopropyl amine oligonucleotides. Nucleic Acids Res. Jan. 25, 1992;20(2):307-14.*

Dapic et al. Antiproliferative activity of G-quartet-forming oligonucleotides with backbone and sugar modifications. Biochemistry. Mar. 19, 2002;41(11):3676-85.*

Ohnuma et al. Inhibitory effects of telomere-mimic phosphorothioate oligonucleotides on various human tumor cells in vitro. Anticancer Res. Jul.-Aug. 1997;17(4A):2455-8.*

Gura T. Systems for identifying new drugs are often faulty. Science. Nov. 7, 1997;278(5340):1041-2.*

Gromeier et al. Viruses for the treatment of malignant glioma. Curr Opin Mol Ther. Oct. 2001;3(5):503-8.*

Johnson et al. Relationships between drug activity in NCI preclinical in vitro and in vivo models and early clinical trials. Br J Cancer. May 18, 2001;84(10):1424-31.*

Bates, Paula J., et al., "Antiproliferative Activity of G-rich Oligonucleotides Correlates with Protein Binding," Journal of Biological Chemistry, vol. 274, No. 37, Sep. 10, 1999, pp. 26369-26377.

Dempsey, Laurie A., et al., "G4 DNA binding by LR1 and its subunits, nucleolin and hnRNP D, a role for G-G pairing in immunoglobulin switch recombination." Journal of Biological Chemistry, vol. 274, No. 2, Jan. 8, 1999, pp. 1066-1071.

Ishikawa, Fuyuki, et al., "Nuclear Proteins that bind the pre-mRNA 3' splice site sequence r(UUAG/G) and the Human Telomeric DNA Sequence d(TTAGGG)n," Molecular and Cellular Biology, Washington, D.C. US, vol. 13, No. 7, Jul. 1, 1993, pp. 4301-4310.

Mata, John E., et al., "A Hexameric Phosphorothioate Oligonucleotide Telomerase Inhibitor Arrests Growth of Burkitt's Lymphoma Cells in Vitro and in Vivo," Toxicology and Applied Pharmacology, 144, 189-197, (1997).

Serin, G., et al., "Two RNA-binding domains determine the RNA-binding specificity of nucleolin." The Journal of Biological Chemistry. United States May 16, 1997, vol. 272, No. 20, pp. 13109-13116.

Weidner, Douglas A., et al., Phosphorothioate oligonucleotides bind in a non sequence-specific manner to the nucleolar protein C23/nucleolin, Febs Letters, vol. 366, No. 2-3, 1995, pp. 146-150.

Ballou, B., et al., "Three-Dimensional Imaging of Nucleolin Trafficking in Normal Cells, Transfectants, and Heterokaryons," SPIE, vol. 2680, pp. 124-31.

US 6,020,459, 02/2000, Barney et al. (withdrawn)

* cited by examiner

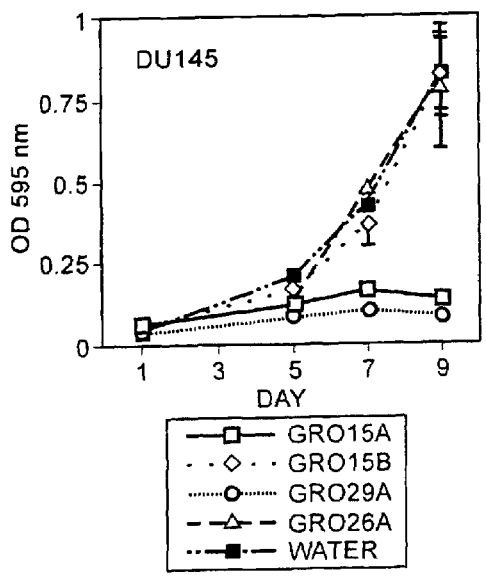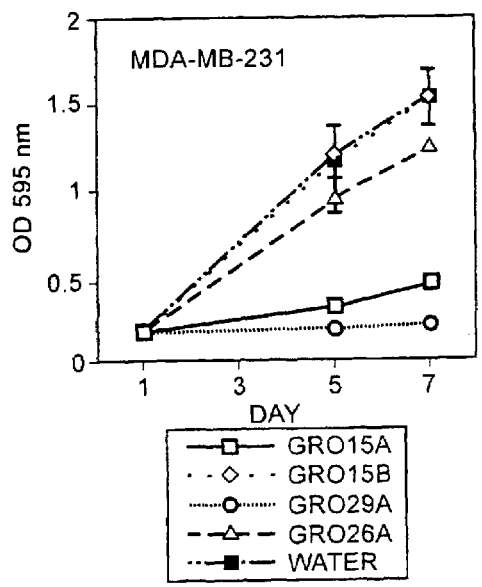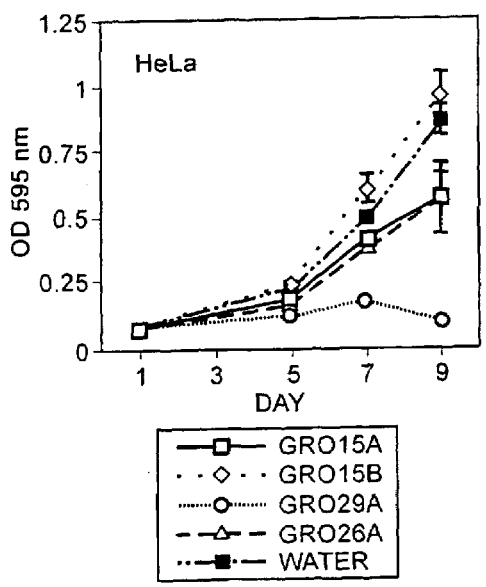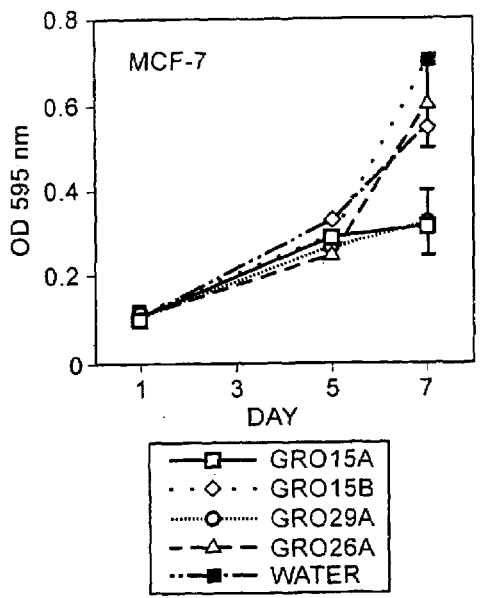

Key:
++, more than 95% growth inhibition
+, partial growth inhibition
N, no growth inhibition MDA is MDA-MB-231
MTX is a methotrexate resistant MCF-7 derivative

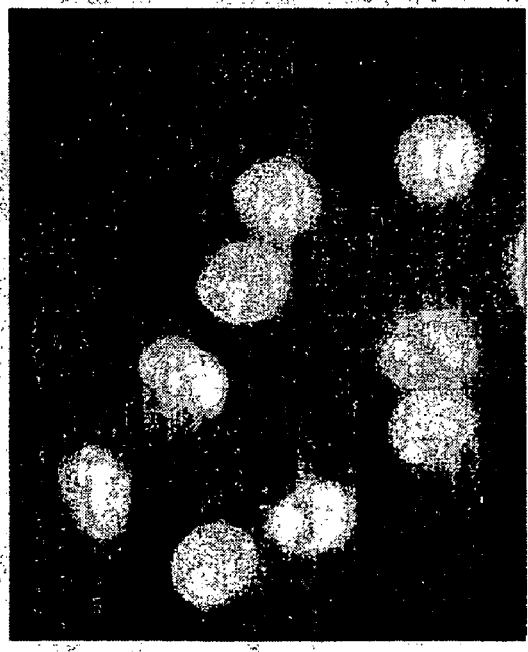
FIG - 10
Untreated Cells (in exponential growth phase)
GRO29A Treated Cells (3 days after addition of GRO29A)

15B: TTGGGGGGGGGTGGGT (Inactive GRO)
29A: TTT(GGT)$_4$TGT(GGT)$_3$GG (Original GRO)
11A (T8): GGTGGTGGTGG
14C (D4): GGTGGTTGTGGTGG
26B (D8): (GGT)$_4$TGT(GGT)$_3$GG
32A (M4): (GGT)$_2$TGT(GGT)$_2$TGT(GGT)$_2$TGTGGTGG
56A (M8): (GGT)$_4$TGT(GGT)$_4$TGT(GGT)$_4$TGT(GGT)$_3$GG

ANTIPROLIFERATIVE ACTIVITY OF G-RICH OLIGONUCLEOTIDES AND METHOD OF USING SAME TO BIND TO NUCLEOLIN

This application is the U.S. national stage of international application PCT/US00/09311 filed 7 Apr. 2000, which claims benefit of U.S. provisional application 60/128,316, filed 8 Apr. 1999, and 60/149,823 filed 19 Aug. 1999.

GRANT REFERENCE

This research was supported by Department of Defense (CDMRP) Prostate Cancer Initiative Grant # DAMD-17-98-1-8583.

FIELD OF THE INVENTION

The present invention relates to inhibiting cell proliferation. Specifically, the present invention relates to specific oligonucleotides which inhibit cell proliferation, including that of neoplastic and/or dysplastic cells, by binding to specific proteins associated with cell proliferation.

BACKGROUND OF THE INVENTION

Oligonucleotides have the potential to recognize unique sequences of DNA or RNA with a remarkable degree of specificity. For this reason they have been considered as promising candidates to realize gene specific therapies for the treatment of malignant, viral and inflammatory diseases. Two major strategies of oligonucleotide-mediated therapeutic intervention have been developed, namely, the antisense and antigene approaches. The antisense strategy aims to down-regulate expression of a specific gene by hybridization of the oligonucleotide to the specific mRNA, resulting in inhibition of translation. Gewirtz et al. (1998) Blood 92, 712-736; Crooke (1998) Antisense Nucleic Acid Drug Dev. 8, 115-122; Branch (1998) Trends Biochem. Sci. 23, 45-50; Agrawal et al. (1998) Antisense Nucleic Acid Drug Dev. 8, 135-139. The antigene strategy proposes to inhibit transcription of a target gene by means of triple helix formation between the oligonucleotide and specific sequences in the double-stranded genomic DNA. Helene et al. (1997) Ciba Found. Symp. 209, 94-102. Clinical trials based on the antisense approach are now showing that oligonucleotides can be administered in a clinically relevant way and have few toxic side effects. Gewirtz et al. (1998) Blood 92, 712-736; Agrawal et al. (1998) Antisense Nucleic Acid Drug Dev. 8, 135-139.

Whereas both the antisense and antigene strategies have met with some success, it has become clear in recent years that the interactions of oligonucleotides with the components of a living organism go far beyond sequence-specific hybridization with the target nucleic acid. Recent studies and reexamination of early antisense data have suggested that some of the observed biological effects of antisense oligonucleotides cannot be due entirely to Watson-Crick hybridization with the target mRNA. In some cases, the expected biological effect (e.g. inhibition of cell growth or apoptosis) was achieved, but this was not accompanied by a down regulation of the target protein and was thus unlikely to be a true antisense effect. White et al. (1996) Biochem. Biophys. Res. Commun. 227, 118-124; Dryden et al. (1998) J. Endocrinol. 157, 169-175. In many cases, it was demonstrated that other non-sequence specific oligonucleotides could exert biological effects that equaled or exceeded the antisense sequence. Barton et al. (1995) Br. J. Cancer 71, 429-437; Burgess et al. (1995) Proc. Natl. Acad. Sci. U.S.A. 92, 4051-4055; Benimetskaya et al. (1997) Nucleic Acids Res. 25, 2648-2656. Though there is currently a high awareness among antisense investigators of the importance of appropriate control oligonucleotides, and the necessity of demonstrating inhibition of target protein production (Stein (1998) Antisense Nucleic Acid Drug Dev. 6, 129-132), the mechanism of non-antisense effects is poorly understood.

In particular, phosphodiester and phosphorothioate oligodeoxynucleotides containing contiguous guanosines (G) have been repeatedly found to have non-antisense effects on the growth of cells in culture. Burgess et al. (1995) Proc. Natl. Acad. Sci. U.S.A. 92, 4051-4055; Benimetskaya et al. (1997) Nucleic Acids Res. 25, 2648-2656; Saijo et al. (1997) Jpn. J. Cancer Res. 88, 26-33. There is evidence that this activity is related to the ability of these oligonucleotides to form stable structures involving intramolecular or intermolecular G-quartets. Burgess et al. (1995) Proc. Natl. Acad. Sci. U.S.A. 92, 4051-4055; Benimetskaya et al. (1997) Nucleic Acids Res. 25, 2648-2656. These are square planar arrangements of four hydrogen-bonded guanines that are stabilized by monovalent cations. Such structures are thought to play an important role in vivo and putative quartet forming sequences have been identified in telomeric DNA (Sundquist et al. (1989) Nature 342, 825-829), immunoglobulin switch region sequences (Sen et al. (1988) Nature 334, 364-366), HIV1 RNA (Sundquist et al. (1993) Proc. Natl. Acad. Sci. U.S.A. 90, 3393-3397), the fragile X repeat sequences (Fry et al (1994) Proc. Natl. Acad. Sci. U.S.A. 91, 4950-4954) and the retinoblastoma gene (Murchie et al. (1992) Nucleic Acids Res. 20, 49-53).

It has been suggested that non-antisense effects may be due to sequestration of intracellular or surface proteins by the oligonucleotide. Gold et al. (1995) Annu. Rev. Biochem. 64, 763-797; Stein (1997) Ciba Found. Symp. 209, 79-89. For G-rich oligonucleotides that can form folded, G-quartet containing structures, this binding is thought to be mediated not by recognition of the primary sequence of the oligonucleotides, but rather of their unique three-dimensional shapes. However, the protein targets of these oligonucleotides have not been well characterized.

Oligonucleotides are polyanionic species that are internalized in cells, probably by receptor-mediated endocytosis. Vlassov et al. (1994) Biochim. Biophys. Acta 1197, 95-108. They are likely to interact with many biomolecules within the cell and also in the extracellular membrane by virtue of both their charge and their shape, as well as sequence-specific interactions. The proteins that bind to oligonucleotides and mediate non-antisense effects have not yet been unequivocally identified.

The present application identifies a G-rich oligonucleotide binding protein, and the ability of a G-rich oligonucleotide to bind to this protein is correlated with its propensity to form G-quartets, and with its ability to inhibit the growth of tumor cells.

Applicants have described G-rich oligonucleotides (GROs) that have potent growth inhibitory effects that are unrelated to any expected antisense or antigene activity. While the mechanism of these effects has not yet been specifically delineated, Applicants have demonstrated that the antiproliferative effects of these oligonucleotides are related to their ability to bind to a specific cellular protein. Because the GRO binding protein is also recognized by anti-nucleolin antibodies, Applicants have concluded that this protein is either nucleolin itself, or a protein of a similar size that shares immunogenic similarities with nucleolin.

Nucleolin is an abundant multifunctional 110 kDa phosphoprotein thought to be located predominantly in the nucleolus of proliferating cells (for reviews, see Tuteja et al. (1998) *Crit. Rev. Biochem. Mol. Biol.* 33, 407-436; Ginisty et al. (1999) *J. Cell Sci.* 112, 761-772). Nucleolin has been implicated in many aspects of ribosome biogenesis including the control of rDNA transcription, pre-ribosome packaging and organization of nucleolar chromatin. Tuteja et al. (1998) *Crit. Rev. Biochem. Mol. Biol.* 33, 407-436; Ginisty et al. (1999) *J. Cell Sci.* 112, 761-772; Ginisty et al. (1998) *EMBO J.* 17, 1476-1486. Another emerging role for nucleolin is as a shuttle protein that transports viral and cellular proteins between the cytoplasm and nucleus/nucleolus of the cell. Kibbey et al. (1995) *J. Neurosci. Res.* 42, 314-322; Lee et al. (1998) *J. Biol. Chem.* 273, 7650-7656; Waggoner et al. (1998) *J. Virol.* 72, 6699-6709. Nucleolin is also implicated, directly or indirectly, in other roles including nuclear matrix structure (Gotzmann et al. (1997) *Electrophoresis* 18, 2645-2653), cytokinesis and nuclear division (Léger-Silvestre et al. (1997) *Chromosoma* 105, 542-52), and as an RNA and DNA helicase (Tuteja et al. (1995) *Gene* 160, 143-148). The multifunctional nature of nucleolin is reflected in its multi-domain structure consisting of a histone-like N-terminus, a central domain containing RNA recognition motifs, and a glycine/arginine rich C-terminus. Lapeyre et al. (1987) *Proc. Natl. Acad. Sci. U.S.A.* 84, 1472-1476. Levels of nucleolin are known to relate to the rate of cellular proliferation (Derenzini et al. (1995) *Lab. Invest.* 73, 497-502; Roussel et al. (1994) *Exp. Cell Res.* 214, 465-472.), being elevated in rapidly proliferating cells, such as malignant cells, and lower in more slowly dividing cells. For this reason, nucleolin is an attractive therapeutic target.

Although considered a predominantly nucleolar protein, the finding that nucleolin was present in the plasma membrane is consistent with several reports identifying cell surface nucleolin and suggesting its role as a cell surface receptor. Larrucea et al. (1998) *J. Biol. Chem.* 273, 31718-31725; Callebout et al. (1998) *J. Biol. Chem.* 273, 21988-21997; Semenkovich et al. (1990) *Biochemistry* 29, 9708; Jordan et al. (1994) *Biochemistry* 33, 14696-14706.

Previously, several mechanisms were proposed to explain the non-sequence-specific effects of oligonucleotides. These included binding to cellular receptors (Rockwell et al. (1997) *Proc. Natl. Acad. Sci. U.S.A.* 94, 6523-6528; Coulson et al. (1996) *Mol. Pharmacol.* 50, 314-325), modulation of cytokine or growth factor activity (Hartmann et al. (1996) *Mol. Med.* 2, 429-438; Sonehara et al. (1996) *J. Interferon Cytokine Res.* 16, 799-803; Fennewald et al. (1995) *J. Biol. Chem.* 270, 21718-21721; Guvakova et al. (1995) *J. Biol. Chem.* 270, 2620-2627; Scaggiante et al. (1998) *Eur. J. Biochem.* 252, 207-215), inhibition of cell cycle progression (Burgess et al. (1995) *Proc. Natl. Acad. Sci. U.S.A.* 92, 4051-4055), changes in cell adhesion (Saijo et al. (1997) *Jpn. J. Cancer Res.* 88, 26-33) and binding to an uncharacterized 45 kDa protein (Rananathan et al. (1994) *J. Biol. Chem.* 269, 24564-24574). The immunostimulatory properties of oligonucleotides containing 5'-CG-3' sequences have also been described (McCluskie et al. (1998) *J. Immunol.* 161, 4463-4466), but it seems unlikely that they are related to the effects Applicants have observed.

In this present application, Applicants have identified an oligonucleotide binding protein and shown a correlation between binding to this protein and antiproliferative activity for a series of G-rich oligonucleotides. These findings are strongly suggestive of a mechanistic role for this protein in non-antisense oligonucleotide-mediated inhibition of cell growth. The basis for recognition of GROs by nucleolin is not obvious from the sequences of the oligonucleotides tested, but may relate to their propensity to form particular G-quartet structures.

The relationship between nucleolin binding and antiproliferative activity for other, non-G-rich, oligonucleotides has not yet been fully evaluated. One mixed sequence oligonucleotide (MIX1) was found to bind nucleolin, although it had no growth inhibitory effect. Nucleolin contains RNA binding domains that can recognize specific sequences of RNA or single-stranded DNA. Dickinson et al. (1995) *Mol. Cell. Biol.* 15, 456-465; Ghisolfi et al. (1996) *J. Mol. Biol.* 260, 34-53. It is possible that this particular oligonucleotide contains a sequence or structure that resembles such a recognition element.

In support of the Applicants' findings that nucleolin binds to G-rich oligonucleotides, recent reports have demonstrated that nucleolin can bind to other G-quartet forming sequences, such as immunoglobulin switch regions and ribosomal gene sequences (Dempsey et al. (1999) *J. Biol. Chem.* 274, 1066-1071 and Hanakai et al. (1999) *J. Biol. Chem.* 274, 15903-15912). It is possible that nucleolin has currently undefined functions in vivo that depend on recognition of G-rich sequences in, for example, ribosomal DNA switch region sequences or telomeres.

The synthesis of nucleolin is positively correlated with increased rates of cell division, and nucleolin levels are therefore higher in tumor cells as compared to most normal cells. In fact, nucleolin is one of the nuclear organizer region (NOR) proteins whose levels, as measured by silver staining, are assessed by pathologists as a marker of cell proliferation and an indicator of malignancy. Nucleolin is thus a tumor-selective target for therapeutic intervention, and strategies to reduce the levels of functional nucleolin are expected to inhibit tumor cell growth.

The consequences of nucleolin inhibition on the growth of cells have not been well studied, but inhibition of a protein whose functions include ribosome production, nuclear transport and cell entry should have profound effects on the growth of cells.

SUMMARY OF THE INVENTION

The present invention provides a method for inhibiting the proliferation of malignant, dysplastic, and/or hyperproliferative cells in a subject by administering to the subject a therapeutically effective amount of a guanosine rich oligonucleotide.

The present invention also provides oligonucleotides which are capable of being specifically bound to a specific cellular protein which is implicated in the proliferation of cells, specifically malignant, dysplastic, and/or hyperproliferative cells.

The present invention also provides methods of screening for molecules or compounds capable of binding to G-rich oligonucleotide binding proteins.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

FIG. 1: MTT assays showing the growth of tumor cells treated with G-rich oligonucleotides or water as a control over time, wherein (A) the cell type is DU145, (B) the cell type is MDA-MB-231, (C) the cell type is HeLa, and (D) the cell type is MCF-7 and wherein □ GRO15A, ◊GRO15B, ○ GRO29A, Δ GRO26A, and ⊞water.

FIG. 10 illustrates the results of immunofluoresence studies showing anti-nucleolin staining of MDA-MB-231 cells untreated (A) and treated (B) with GRO29A 72 hours after treatment.

FIG. 14: A photograph depicting the results of an electrophoretic mobility shift assay for screening nucleolin-binding compounds wherein:

| Lane | Description |
| --- | --- |
| 1. GRO15B | Inactive G-rich oligonucleotide |
| 2. GRO29A | Antiproliferative G-rich oligonucleotide |
| 3. Caffeine | Stimulant; cAMP phosphodiesterase inhibitor |
| 4. 5-Fluorouracil | Nucleoside analog; cancer drug; DNA damaging agent |
| 5. Cisplatin | Cancer drug; DNA crosslinker |
| 6. Polymyxin B sulfate | Polypeptide; antibiotic |
| 7. Ara-C | Nucleotide analog; cancer drug; DNA damaging agent |
| 8. Camptothecin | Natural product; cancer drug; topoisomerase I inhibitor |
| 9. PMA | Phorbol ester; tumor promoter; PKC activator |
| 10. Taxol | Natural product; cancer drug; anti-mitotic |
| 11. Doxorubicin (adriamycin) | Antitumor antibiotic; DNA binding agent |
| 12. Heparin | Polyanionic polysaccharide |
| 13. OMR29A | G-rich oligo with modified backbone; antiproliferative |

DETAILED DESCRIPTION OF THE INVENTION

The present invention provides novel guanine rich oligonucleotides (GROs) and methods of using at least one GRO to inhibit the growth of neoplastic, dysplastic, or otherwise hyperproliferative cells in a subject.

Examples of the novel oligonucleotides of the present invention have the following nucleotide sequences and are designated GRO14A (5'-GTTGTTTGGGGTGG-3' SEQ ID No: 1), GRO15A (5'-GTTGTTTGGGGTGGT-3' SEQ ID No: 2), GRO25A (5'-GGT-TGGGGTGGGTGGGGTGGGTGGG-3' SEQ ID No: 3), GRO28A (5'-TTTGGTGGTGGTGGTTGTGGTGGT-GTG-3' SEQ ID No: 4), GRO29A (5'-TTTGGTGGTGGTG-GTTGTGGTGGTGGTGG-3' SEQ ID No: 5), GRO29-2 (5'-TTTGGTGGTGGTGGTTTTGGTGGTGGTGG-3' SEQ ID No: 6), GRO29-3 (5'-TTTGGTGGTGGTGGTGGTG-GTGGTGGTGG-3' SEQ ID No: 7), GRO29-5 (5'-TTTG-GTGGTGGTGGTTTGGGTGGTGGTGG-3' SEQ ID No: 8), GRO29-13 (5'-TGGTGGTGGTGGT-3' SEQ ID No: 9), GRO11A (5'-GGTGGTGGTGG-3' SEQ ID No: 10), GRO14C (5'-GGTGGTTGTGGTGG-3' SEQ ID No: 11), GRO26B (5'-GGTGGTGGTGGTTGTGGTGGTGGTGG-3' SEQ ID No: 12), GRO56A (5'-GGTGGTGGTGGT-TGTGGTGGTGGTGGTTGTGGTGGTGGTG-GTTGTGGTGGTGGTGG-3' SEQ ID No: 13), GRO32A (5'-GGTGGTTGTGGTGGTTGTGGTGGTTGTGGTGG-3' SEQ ID No: 14), GRO32B (5'-TTTGGTGGTGGTGGT-TGTGGTGGTGGTGGTTT-3' SEQ ID No: 15), GRO29-6 (5'-GGTGGTGGTGQTTGTGGTGGTGGTGGTTT-3' SEQ ID No: 16), GRO28B (5'-TTTGGTGGTGGTGGTGtG-GTGGTGGTGG-3' SEQ ID No: 17), and GRO13A (5'-TGGTGGTGGT-3' SEQ ID No: 18). Other oligonucleotides having the same activity are also contemplated.

Figure 3:
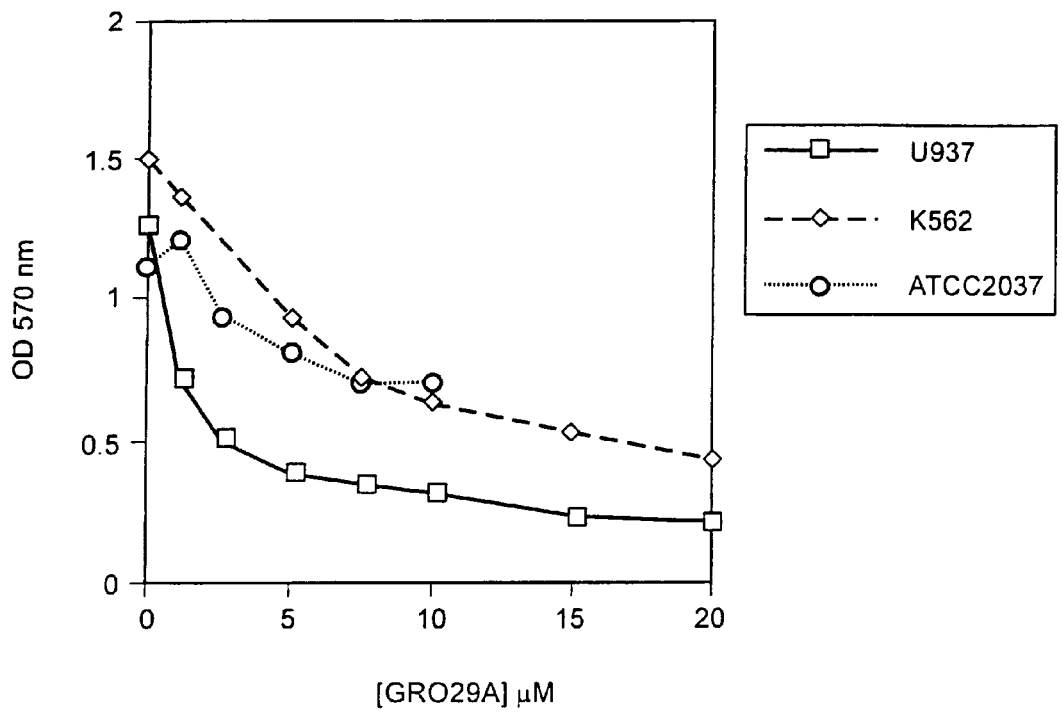
FIG. 3: MTT assays showing the dose dependence of growth inhibition by GRO29A for leukemic cell lines, U937 and K563, and a non-malignant mouse hematopoietic stem cell line (ATCC 2037).

Oligonucleotides GRO29-2, GRO29-3, GRO29-5, GRO29-13, GRO15C, GRO28H and GRO24I have been shown to inhibit the growth of breast cancer cells and/or to compete for binding to the G-rich oligonucleotide binding protein as shown by an electrophoretic mobility shift assay (see FIGS. 6 and 7). Demonstration of activity and protein binding of GROs of the present invention include GRO15A, 29A are shown in FIG. 1 and FIG. 6; GRO14A, 25A, 28A are shown in FIG. 7; GRO11A, 14C, 26B, 32A, 56A are shown in FIG. 3; GRO29-2, 29-3, 29-5, 29-6, 28B have also been shown to have antiproliferative activity and protein binding.

By G-rich oligonucleotide (GRO) it is meant that the oligonucleotides consist of 4-100 nucleotides (preferably 10-30 nucleotides) with DNA, RNA, 2'-O-methyl, phosphorothioate or other chemically similar backbones. Their sequences contain one or more GGT motifs. The oligonucleotides have antiproliferative activity against cells and bind to GRO binding protein and/or nucleolin. These properties can be demonstrated using the MTT assay and the EMSA technique shown in FIG. 6B, or other similar assays.

The oligonucleotides of the present invention are rich in guanosine and are capable of forming G-quartet structures. Specifically, the oligonucleotides of the present invention are primarily comprised of thymidine and guanosine with at least one contiguous guanosine repeat in the sequence of each oligonucleotide. The G-rich oligonucleotides are stable and can remain undegraded in serum for prolonged periods of time and have been found to retain their growth inhibiting effects for periods of at least seven days.

As used herein, the term "oligonucleotide" is defined as a molecule comprising two or more deoxyribonucleotides or ribonucleotides. The exact size depends on a number of factors including the specificity and binding affinity to target ligands. In referring to "bases" or "nucleotides," the terms include both deoxyribonucleic acids and ribonucleic acids.

The novel oligonucleotides of the present invention can be used to inhibit the proliferation of malignant, dysplastic and/or hyperproliferative cells by specifically binding to specific cellular proteins associated with cell proliferation including nucleolin and nucleolin-like proteins.

The term "nucleolin-like" is used to define a protein that is either nucleolin itself or a protein of similar size that shares immunogenic similarities and/or functional similarities with nucleolin.

The oligonucleotides can be modified at their 3' end in order to alter a specific property of the oligonucleotide. For example, the 3'-terminus of the oligonucleotide can be modified by the addition of a propyl amine group which has been found to increase the stability of the oligonucleotide to serum nucleases. Other modifications that are well known in the art include 3' and 5' modifications, for example, the binding of cholesterol, and backbone modifications, for example, phosphorothioate substitution and/or 2'-O-methyl RNA.

The term "inhibition of the proliferation of malignant, dysplastic, and/or hyperplastic cells" includes any partial or total growth inhibition and includes decreases in the rate of proliferation or growth of the cells.

As used herein, the term "neoplastic" includes the new, abnormal growth of tissues and/or cells, such as a cancer or tumor, including, for example, breast cancer, leukemia or prostate cancer. The term "neoplastic" also includes malignant cells which can invade and destroy adjacent structures and/or metastasize.

As used herein, the term "dysplastic" includes any abnormal growth of cells, tissues, or structures including conditions such as psoriasis.

The term "subject" means all animals including humans. Examples of subjects include humans, cows, dogs, cats, goats, sheep, and pigs.

Those skilled in the art are easily able to identify patients having a malignant, dysplastic, or a hyperproliferative condition such as a cancer or psoriasis, respectively. For example, patients who have a cancer such as breast cancer, prostate cancer, cervical carcinomas, and the like.

A therapeutically effective amount is an amount of an oligonucleotide of the present invention, that when administered to the subject, ameliorates a symptom of the disease, disorder, or condition, such as by inhibiting or reducing the proliferation of dysplastic, hyperproliferative, or malignant cells.

The GROs of the present invention can be administered to a patient or subject either alone or as part of a pharmaceutical composition. The GROs can be administered to patients either orally, rectally, parenterally (intravenously, intramuscularly, or subcutaneously), intracisternally, intravaginally, intraperitonally, intravesically, locally (powders, ointments, or drops), or as a buccal or nasal spray.

Compositions of the GROs of the present invention suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound (GRO) is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a GRO of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

In addition, the GROs of the present invention can exist in unsolvated as well as solvated forms with pharmaceutically acceptable solvents such as water, ethanol, and the like. In general, the solvated forms are considered equivalent to the unsolvated forms for the purposes of the present invention.

The GROs of the present invention can be administered to a patient at dosage levels in the range of about 1.5 mg to about 150 mg per day. For a normal human adult having a body weight of about 70 kilograms, a dosage in the range of about 0.2 mg to about 2.0 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art. The GROs of the present invention can be given in single and/or multiple dosages.

In addition, it is intended that the present invention cover GROs made either using standard organic synthetic techniques, including combinatorial chemistry or by biological methods, such as through metabolism.

The G-rich oligonucleotides of the present invention may also be used in combination with other chemotherapeutic agents to provide a synergistic or enhanced efficacy or inhibition of neoplastic cell growth. For example, the G-rich oligonucleotides of the present invention can be administered in combination with chemotherapeutic agents including, for example, cis-platin, mitoxantrone, etoposide, camptothecin, 5-fluorouracil, vinblastine, paclitaxel, docetaxel, mithramycin A, dexamethasone, caffeine, and other chemotherapeutic agents well known to those skilled in the art. Experiments carried out by Applicants showed that GRO29A acts synergistically with cis-platin in inhibiting MDA-MB-231 cell growth in vitro. Applicants fund that under conditions in which GRO29A has little effect by itself (5% growth inhibition), a combination of cis-platin (0.5 µg/ml) and GRO29A synergistically inhibited cell growth (63% inhibition as compared to 29% inhibition for cis-platin alone).

Additionally, the present invention provides a method for selecting oligonucleotides that bind to G-rich oligonucleotide binding proteins. The method utilizes an electrophoretic mobility shift assay (EMSA), as described below, to screen for oligonucleotides that bind strongly to the specific protein and which, therefore, would be expected, according to the present invention, to have antiproliferative activity. Oligonucleotides to be screened as potential antiproliferative agents are labeled and then incubated with nuclear extracts in the absence or presence of unlabeled competitor oligonucleotide and are allowed to react. The reaction mixtures are then electrophoresed and mobility shifts and/or bond intensity can be used to identify those oligonucleotides which have bound to the specific protein.

Figure 6A:
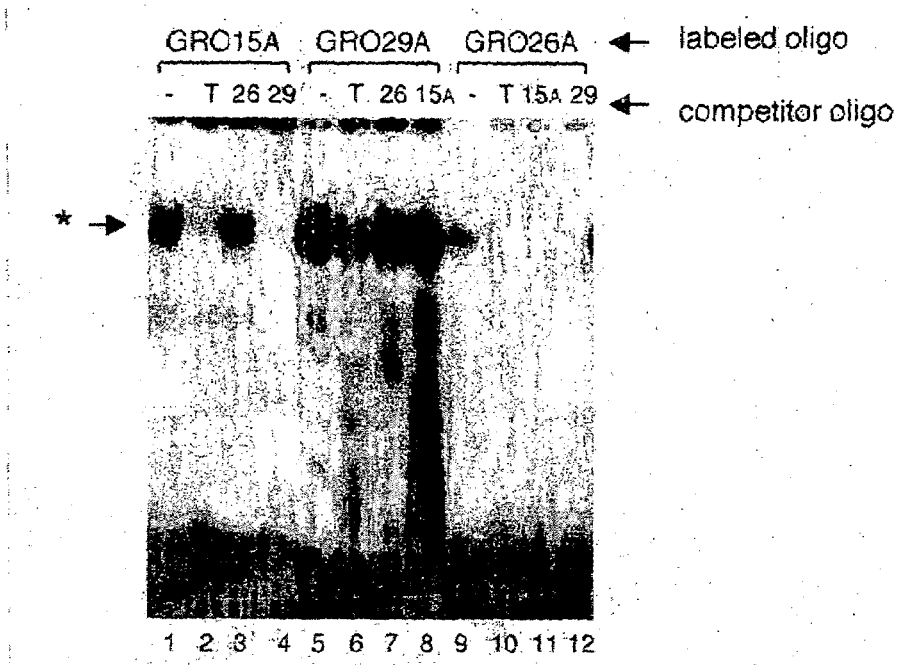
FIG. 6: (A) Electrophoretic mobility shift assay (EMSA) showing binding of $^{32}$P-labeled oligonucleotides to 5 µg HeLa nuclear extracts and competition by unlabeled competitor oligonucleotides (100-fold molar excess over labeled oligonucleotide). Competitor oligonucleotides are abbreviated to T (TEL), 29 (GRO29A), 26 (GRO26A) and 15A (GRO15A). (B) EMSA showing complexes formed between $^{32}$P-labeled TEL oligonucleotide (1 nM) and 5 µg HeLa nuclear extracts, and the effect of unlabeled competitor G-rich oligonucleotides (10 or 100 nM). (C) SDS-polyacrylamide gel showing complexes formed by UV crosslinking of labeled oligonucleotides and HeLa nuclear extracts incubated in the absence or presence of unlabeled competitor (100-fold molar excess). (D) Southwestern blot of HeLa nuclear extracts probed with $^{32}$P-labeled G-rich oligonucleotides ($2\times10^6$ counts per min, approximately 0.75 mmol).
Figure 6B:
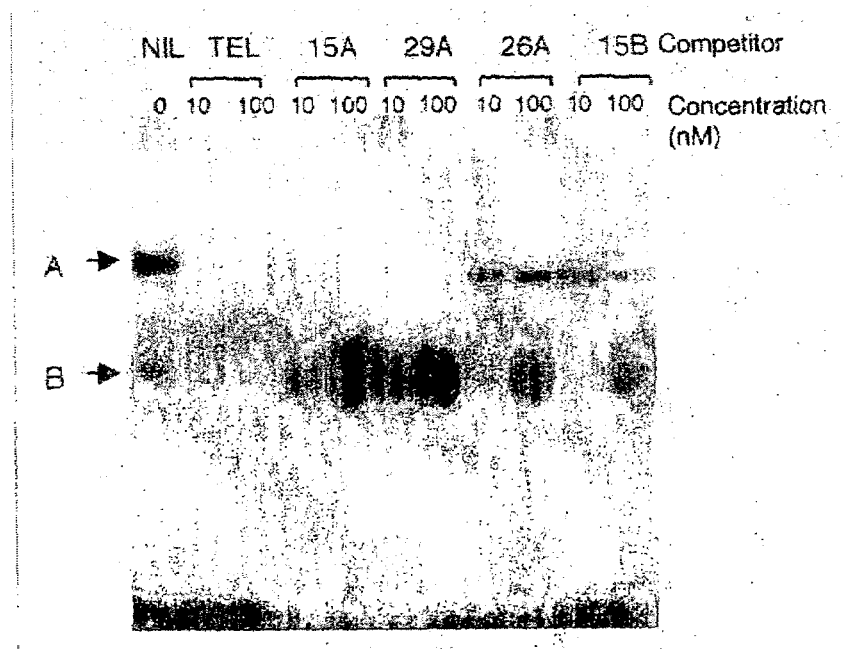

Alternatively, unlabeled compounds to be screened are incubated with nuclear extracts in the presence of labeled oligonucleotide (for example 5'-TTAGGGTTAGGG TTAGGG TTAGGG (SEQ ID NO: 20)) and binding is assessed by a decrease in the intensity of the shifted band, as in FIG. 6B.

Alternatively, compounds to be screened can be added to cells growing in culture. Potential antiproliferative agents will be identified as those which cause an altered intensity and localization of nucleolin, as detected by immunofluorescence microscopy, as shown in FIG. 10.

The examples presented below are intended to illustrate particular embodiments of the invention and are not intended to limit the scope of the specification, including the claims, in any way.

EXAMPLES

Experimental Procedures

Oligonucleotides. 3'-modified oligonucleotides were purchased from Oligos Etc. (Wilsonville, Oreg.) or synthesized at the University of Alabama at Birmingham using 3'-C3-amine CPG columns from Glen Research (Sterling, Va.). Unmodified oligonucleotides were obtained from Life Technologies, Inc., Gaithersburg, Md. Oligonucleotides were resuspended in water, precipitated in n-butyl alcohol, washed with 70% ethanol, dried and resuspended in sterile water or phosphate buffered saline (PBS). They were then sterilized by filtration through a 0.2 µm filter. Each oligonucleotide was checked for integrity by 5'-radiolabeling followed by polyacrylamide gel electrophoresis (PAGE). The results reported in this paper were reproducible and independent of the source of synthetic oligonucleotides.

Cell growth assays. Cells were plated at low density ($10^2$ to $10^3$ cells per well, depending on cell line) in the appropriate serum-supplemented medium in 96-well plates (one plate per MTT assay time point) and grown under standard conditions of cell culture. The following day (day 1) oligonucleotide, or water as control, was added to the culture medium to give a final concentration of 15 µM. Further oligonucleotide, equivalent to half the initial dose, was added to the culture medium on days two, three and four. Cells were assayed using the MTT assay (Morgan (1998) Methods. Mol. Biol. 79, 179-183) on days one, three, five, seven and nine after plating. The culture medium was not changed throughout the duration of the experiment (which was the time required for untreated cells to grow to confluence). Experiments were performed in triplicate and bars represent the standard error of the data. For the experiment shown in FIG. 7A, MDA-MB-231 breast cancer cells ($5 \times 10^2$ cells per well) were plated in a 96-well plate. After twenty-four hours, a single dose of oligonucleotide, or equal volume of PBS as a control, was added to the culture medium to a final concentration of 10 µM. Viable cells were assessed seven days after plating using the MTT assay. For the experiment using 3'-unmodified oligonucleotides (FIG. 7D), serum-supplemented medium was replaced by serum-free medium containing oligonucleotide (or serum-free medium alone in control wells). After incubation at 37° C. for four hours, fetal calf serum (Life Technologies, Inc.) was added to the medium to give 10% v/v. Heparin used in these experiments was USP grade sodium salt derived from porcine intestine, purchased from Apothecon (Bristol-Myers Squibb Co.). Working solutions were diluted from the stock (1000 units/ml) in sterile PBS.

Detection of G-quartets by U.V. Spectroscopy. Oligonucleotides were resuspended in Tm buffer (20 mM Tris HCl, pH 8.0, 140 mM KCl, 2.5 mM $MgCl_2$) at a concentration such that $A_{260}$=0.6 (molar concentrations ranged from 2.0 to 3.9 µm). Samples were annealed by boiling for five minutes and allowing to cool slowly to room temperature and overnight incubation at 4° C. Thermal denaturation/renaturation experiments were carried out using an Amersham Pharmacia Biotech Ultrospec 2000 instrument equipped with a Peltier effect heated cuvette holder and temperature controller (Amersham Pharmacia Biotech). Absorbance at 295 nm was monitored over a temperature range of 25-95 or 20-90° C. at a heating/cooling rate of 0.5° C./min.

Oligonucleotide Uptake. MDA-MB-231 cells were seeded in twenty-four well plates at a density of $5 \times 10^5$ cells/well. After twenty-four hours, oligonucleotide (5 nmol of unlabeled oligonucleotide and $5 \times 10^6$ cpm (approximately 1 µmol) of 5'-$^{32}$P-labeled oligonucleotide) was added directly to the culture medium to give a final concentration of 10 µM. Cells were incubated at 37° C. for ten or twenty-six hours and were then washed three times with PBS. Cells were removed from the plate by trypsinization, washed, and collected in 100 µl of PBS. A 50-µl aliquot was counted by scintillation counting to assess cell-associated radioactivity. To ensure that the washing procedures were sufficient to remove all excess oligonucleotide, the final PBS wash was counted and found to be very low compared with the cell-associated radioactivity. The remaining 50-µl aliquots were boiled for five minutes and placed on ice. An equal volume of phenol/chloroform was added, and the oligonucleotides were extracted in the aqueous phase, precipitated with n-butyl alcohol, and analyzed by denaturing polyacrylamide gel electrophoresis on a 15% gel.

Electrophoretic mobility shift assays (EMSAs). Oligonucleotides were 5'-labeled with $^{32}$P using T4 kinase. Labeled oligonucleotide (final concentration 1 nM, approximately 50,000 cpm) was preincubated for thirty minutes at 37° C. either alone or in the presence of unlabeled competitor oligonucleotide. Nuclear extracts were added, and the sample was incubated a further thirty minutes at 37° C. Both the preincubation and binding reactions were carried out in Buffer A (20 mM Tris.HCl pH 7.4, 140 mM KCl, 2.5 mM $MgCl_2$, 1 mM dithiothreitol, 0.2 mM phenylmethyl sulfonyl fluoride and 8% (v/v) glycerol). Electrophoresis was carried out using 5% polyacrylamide gels in TBE buffer (90 mM Tris borate, 2 mM EDTA).

U.V. Cross Linking. For the UV crosslinking experiments, samples were incubated as described above (EMSA). They were then placed on ice and irradiated at 5 cm from the source using the "autocross link" function of a Stratagene UV Stratalinker. Following irradiation, samples were electrophoresed under denaturing conditions on a 8% polyacrylamide-SDS gel using a standard Tris glycine buffer and visualized by autoradiography.

Southwestern Blotting. Nuclear extracts were electrophoresed on a 8% polyacrylamide-SDS gel and transferred to polyvinylidene difluoride (PVDF) membrane by electroblotting using a Tris glycine/methanol (10% v/v) buffer. Immobilized proteins were denatured and renatured by washing for thirty minutes at 4° C. with 6 M guanidine. HCl followed by washes in 1:1, 1:2 and 1:4 dilutions of 6M guanidine in HEPES binding buffer (25 mM HEPES pH 7.9, 4 mM KCl, 3 mM $MgCl_2$). The membrane was blocked by washing for one hour in a 5% solution of non-fat dried milk (NDM) in binding buffer. Hybridization was labeled oligonucleotide (1-4×$10^6$ cpm) took place for two hours at 4° C.

in HEPES binding buffer supplemented with 0.25% NDM, 0.05% Nonidet P 40, 400 µg/ml salmon sperm DNA and 100 µg/ml of an unrelated, mixed sequence 35-mer oligonucleotide (5'-TCGAGAAAAACTCTCCTCTCCTTCCTTC-CTCTCCA-3' SEQ ID No: 19). Membranes were washed in binding buffer and visualized by autoradiography.

Western Blotting. Western blotting was carried out at room temperature in PBS buffer containing Tween 20 at 0.1% (for polyclonal antibody) or 0.05% (monoclonal antibody). PVDF membranes were blocked with PBS-Tween 20 containing 5% NDM for one hour, washed and incubated for one hour with a 1:1000 dilution of nucleolin antiserum or nucleolin monoclonal antibody (MBL Ltd., Japan, 1 µg/ml final concentration) in PBS-Tween 20. The membranes were washed three times for five minutes each wash in PBS/Tween 20 and incubated for one hour with secondary antibody diluted in PBS/Tween 20 (1:1000 anti-rabbit IgG-HRP or 1:2000 anti-mouse IgG-HRP). After washing the blot was visualized using ECL reagent (Amersham Pharmacia Biotech) according to the manufacturer's instructions.

Capture of Biotinylated Oligonucleotide-Protein Complexes. MDA-MB-231 cells were grown to 50% confluence in 90 mm dishes. 5'-Biotinylated oligonucleotides were added to the culture medium at a final concentration of 5 µM. After incubation for two hours at 37° C., cells were washed extensively with PBS and lysed by addition of 1 ml of lysis buffer (50 mM Tris.HCl pH 8.0, 150 mM NaCl, 0.02% (w/v) sodium azide, 0.1 mg/ml phenylmethyl sulfonyl fluoride, 1% (v/v) Nonidet P40, 0.5% (w/v) sodium deoxycholate, 0.5 mM dithiothreitol, 1 µg/ml aprotinin) followed by incubation at −20° C. for ten minutes. Genomic DNA was sheared by repeated injection of the lysate through a fine gauge needle. Lysate was added to streptavidin coated magnetic beads (MagneSphere, Promega Inc.) and incubated ten minutes at room temperature. Beads were captured and unbound sample was removed. Beads were then washed twice with 1 ml of lysis buffer and again with 1 ml of Buffer A. Finally, proteins were eluted by addition of 50 µl of loading buffer (containing 1% SDS and 5% 2-mercaptoethanol) and incubation for fifteen minutes at 65° C.

Preparation of Nuclear, Cytoplasmic and Membrane Protein Extracts. HeLa nuclear extracts used in EMSAs were purchased from Promega Inc. (bandshift grade). Nuclear and cytoplasmic extracts from MDA-MB-231 cells were prepared using the protocol described in F. M. Ausubel et al. Ausubel et al. (Eds.) (1996) Current Protocols in Molecular Biology, Wiley, N Y, Section 12.1. Plasma membrane proteins were prepared from MDA-MB-231 cells using a method previously described. Yao et al. (1996) Biochemical Pharmacology 51, 431-436; Naito et al. (1988) J. Biol. Chem. 263, 11887-11891.

India Ink Staining. The membrane was incubated for 15 minutes at room temperature in PBS-Tween 20 containing three drops of Higgins India Ink 4415 and washed with distilled water.

Figure 14:
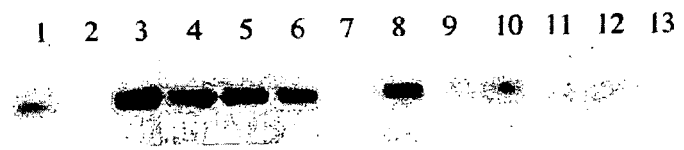

Nucleolin Binding Assay. To determine which non-oligonucleotide-based molecules or compounds are capable of binding to nucleolin, an EMSA was performed as described below and the results of which are shown in FIG. 14. In this assay, the binding ability of several different molecules or compounds for nucleolin was examined. This type of assay can be utilized to screen for molecules or compounds capable of binding nucleolin.

Nuclear proteins (2.5 µg, in this case from HeLa cells) were added to 5'-$^{32}$P-labeled TEL oligonucleotide (5'-TTAGGGTTAGGGTTAGGGTTAGGG SEQ ID No: 20, 2 nM final concentration). Unlabeled competitor oligonucleotide or compound was added to give a final concentration of 50 nM oligonucleotide (equivalent to approximately 0.5 µg/ml for GRO29A) or 0.5 µg/ml (lanes 3-12). Binding reactions took place for 30 minutes at 37° C. in a buffer containing 20 mM Tris.HCl pH 7.4, 140 mM KCl, 2.5 mM MgCl$_2$, 8% (v/v) glycerol, 1 mM DTT, 0.2 mM PMSF). Samples were analyzed on a 5% polyacrylamide gel using TBE buffer.

Chemotherapeutic Agent and GRO Experimental Protocol. Cisplatin (in 1% DMSO solution to give a final concentration of 0.5 µg/ml) was added to the medium of MDA-MB-231 breast cancer cells growing in culture. After two hours, GRO29A (in PBS solution to give a final concentration of 8 µM) was added to the medium. After six days, the relative number of viable cells was determined using the MTT assay. Cells treated with GRO29A alone received an appropriate volume of 1% DMSO in place of cisplatin. Cells treated with cisplatin alone received an appropriate volume of PBS in place of GRO29A.

In Vivo Efficacy of GROs Against Cancer. The primary objective is to demonstrate in vivo efficacy of GROs against prostate cancer, and success in these studies may lead to clinical trials of GROs. The second objective is to examine nucleolin levels and characteristics in prostate cells. Nucleolin, a nucleolar protein involved in multiple aspects of cell growth, has been identified as the putative target for GRO effects. It is Applicants' hypothesis that GROs bind to and inactivate nucleolin. It is known that levels of nucleolin (in the nucleus) are positively correlated with the rate of cell proliferation, and thus, strategies that inhibit nucleolin have significant therapeutic potential. Applicants have shown that nucleolin is also present on the surface of prostate cancer cells, and this may be relevant to the mechanism of GRO effects. In addition, levels of cell surface nucleolin may be elevated in malignant cells compared to normal cells. This would have implications in terms of nucleolin as a tumor cell marker. Another objective is to explore novel therapies for prostate cancer, such as combination therapies of GRO and chemotherapy agents, and small molecule inhibitors of nucleolin.

Determining the activity of GROs in a series of cell lines derived from normal and malignant prostate tissue. Nucleolin levels in the nucleus, cytoplasm and plasma membrane of these cells will be examined using blotting techniques and immunofluorescence microscopy. To optimize delivery of GROs, uptake and activity of GROs introduced to cultured cells by a number of different methods can be studied. Also, tumor uptake of GROs delivered by different methods in mouse and rat models of prostate cancer will be studied. To study in vivo efficacy, nude mice with subcutaneous or orthotopically implanted tumor xenografts and the Dunning rat model of prostate cancer are used. Preliminary data suggests GROs are synergistic with some chemotherapy drugs. Therefore, the effects of combinations of GROs with a variety of cytotoxic and other agents in cultured cells can be examined, and tested for any synergistic combinations in animal models. Finally, a homology model of nucleolin based on the reported structures of many similar proteins can be constructed and used to identify potential small molecule inhibitors of nucleolin by a "virtual screening" method.

Conventional chemotherapy agents have been ineffective in prolonging survival in randomized trials of patients with hormone refractory prostate cancer, and novel therapeutic approaches are urgently required. The GROs of the present invention are potentially tumor-specific agents that are highly active against prostate cancer cells. They have a novel mechanism of action and enormous therapeutic potential in the fight against prostate cancer. Applicants have also identified nucleolin as a new target for therapeutic intervention in prostate cancer. Development of the understanding of this protein can lead to improved diagnostic or prognostic techniques for prostate cancer, or a new class of drugs that inhibit nucleolin.

The methods described below describe the testing of oligonucleotide GRO29A. However, if another GRO has superior activity and similar stability, it could be used in place of GRO29A.

Sensitivity of Various Malignant and Transformed Prostate Cell Lines, and the Relationship Between Sensitivity and Nucleolin/GRO Binding Protein Levels. The $GI_{50}$ value for GRO29A against a variety of cell lines derived from human and rat prostate using the MTT assay is calculated. These will include hormone-dependent (LNCaP) and independent (DU145, PC-3), non-malignant (PZ-HPV-7 and rat YPEN-1), and multidrug resistant (rat AT3 B1 and MLLB-2) cell lines. Cell lines can be purchased from ATCC. To determine nucleolin levels, nuclear, cytoplasmic and plasma membrane extracts are prepared from each cell line by standard methods. Bates et al. (1999) *J. Biol. Chem.* 274 (37):26369-77. Extracts are electrophoresed on 8% polyacrylamide-SDS gels and transferred to PVDF membranes. They are examined by Southwestern blotting (with radiolabeled GRO) and Western blotting (with nucleolin monoclonal antibody, Santa Cruz) to determine levels of GRO-binding protein/nucleolin. Cells are also examined by immunofluorescent staining using nucleolin antibody under appropriate for staining either intracellular or cell surface proteins.

Optimization of Delivery of Oligonucleotides to Tumor Cells in Culture and In Vivo. To investigate the uptake of GRO29A in cultured cells, a 5'-FITC labeled analog of GRO29A is used. Cells (initially DU145 and PC-3) are treated with this oligonucleotide delivered by a variety of different methods. These will include electroporation, cationic lipids (1 μg GRO29A: 4 μg DOTAP-DOPE [1:1]), polymyxin B sulfate (Sigma), lactic acid nanoparticles (a simple synthesis is described in Berton et al. (1999) *Eur. J. Pharm. Biopharm.* 47(2):119-23), and streptolysin O permeabilization (Giles et al. (1998) *Nucleic Acids Res.* 26(7): 1567-75). Oligonucleotide uptake and intracellular localization are assessed by fluorescence microscopy. The effects of different delivery methods on the antiproliferative activity of GRO29A are determined by the MTT assay. To determine whether the uptake characteristics of GRO29A are significantly different from non-G-rich oligonucleotides, the unassisted uptake of GRO29A with C-rich and mixed sequence FITC-labeled oligonucleotides are compared. If uptake is significantly different, investigation of the possibility that different receptors are utilized is carried out in experiments in which FITC labeled oligonucleotides are incubated with cells in the presence of unlabeled competitor oligonucleotides. These experiments provide important information regarding the uptake of oligonucleotides in general, and the importance of GRO interaction with nucleolin at the cell surface.

To examine the pharmacokinetics, stability and tumor delivery in vivo methods similar to those reported previously for a G-rich, phosphodiester oligonucleotide that is being evaluated as an anti-HIV agent are used. Wallace et al. (1997) *J. Phlarmacol. Exp. Ther.* 280(3):1480-8. First, an analog of GRO29A is synthesized that is internally labeled with $^{32}P$. This procedure has been described previously (Bishop et al. (1996) *J. Biol. Chem.* 271(10):5698-703), and involves the synthesis of two short oligonucleotide fragments, 5'-labeling of one fragment using T4 kinase, followed by template-directed ligation of the two fragments by T4 ligase. The labeled oligonucleotide is then purified by polyacrylamide gel electrophoresis (PAGE). Male nude mice (nine in total) are subcutaneously (s.c.) inoculated by their hind flank with DU145 prostate cancer cells under mild anesthesia. When tumors are established (approximately 0.5 cm diameter), the mice are treated with a single 5 mg/kg dose of GRO29A (a mixture of labeled and unlabeled oligonucleotide) in a volume of 25 μl by intratumoral, intraperitoneal or intravenous (tail vein) injection. The animals are observed for evidence of acute toxicity and weight loss. On days two, four and seven after GRO injection, mice are euthanized by $CO_2$ inhalation, the tumor excised, and blood and organs are collected. Levels of radioactivity in the tumor, serum, liver, kidney, spleen and prostate are examined. Stability is determined by denaturing PAGE of serum samples. Similar experiments are also carried out using the Dunning prostatic carcinoma model. Isaacs et al. (1978) *Cancer Res.* 38(11 Pt 2):4353-9; Zaccheo et al. (1998) *Prostate* 35(4):237-42. If any of the delivery techniques Tested in cultured cells result in significantly improved uptake (and are appropriate for in vivo delivery), they are also tested. These experiments determine the optimal administration routes in rats and mice, and provide an indication of the optimal dosing schedule. All animal experiments strictly adhere to institutional guidelines on animal care and use.

Evaluation of the Efficacy of GROs in Inhibiting Prostate Cancer Growth and Metastasis In Vivo. The efficacy in nude mice models is first tested. Mice are inoculated s.c. with DU145 cells under mild anesthesia. After the establishment of palpable xenografts, mice are treated (six mice per group) with GRO29A, control oligonucleotide (5'-GACTGTAC-CGAGGTGCAAGTACTCTA (SEQ ID NO: 21), with 3' amino modification), or PBS using the optimal administration route described above. Three treatment groups receive 0.5, 5 or 50 mg/kg doses twice per week for two weeks. Body weight and tumor size (measured with calipers) are monitored. At an appropriate time, the mice are euthanized by inhalation of $CO_2$ and tumors excised. Sections of the tumor are examined by morphological analysis and immunostaining, including nucleolin, PCNA, Ki 67 and TUNEL analysis for apoptosis. Similar experiments using the optimal (or economically feasible) dose are carried to determine efficacy of GRO29A in inhibiting PC-3 and LNCaP xenografts. Models of metastatic prostate cancer are then implemented. Surgical orthotopic implantation of PC-3 tumors to the prostate glands of nude mice has been reported recently (An et al. (1998) *Prostate* 34(3):169-74), and results in lymph node (13/19 mice) and lung metastases (5/19) by twelve weeks after implantation. The Dunning rat model of prostatic carcinoma was developed by Isaacs et al. ((1978) *Cancer Res.* 38(11 Pt 2):4353-9) and has been widely used to study tumor growth and metastasis. This involves s.c. injection of tumor tissue and results in lymph node, lung and skeletal metastasis. Animals (fifteen per group) are implanted with tumors as described previously (Isaacs et al. (1978) *Cancer Res.* 38(11 Pt 2):4353-9; Zaccheo et al. (1998) *Prostate* 35(4):237-42), and treatment with GRO29A begins six weeks after implantation (or at the first appearance of palpable tumors in the rat model), and continues twice per week for a further six weeks. At this time (or before, if animals appear moribund or distressed), animals are euthanized and subjected to autopsy to examine primary tumor size and metastasis. Tumors and metastases are histologically examined as above.

Evaluation of Combinations GRO-Cytotoxic Drug Therapies for Prostate Cancer. The efficacy of combination treatments of GRO29A with chemotherapy drugs and other agents expected to affect growth-arrested cells are determined. These include mitoxantrone, etoposide, cis-platin, camptothecin, 5-fluorouracil, vinblastine, mithramycin A, dexamethasone, and caffeine (promotes progression through S phase cell cycle checkpoints). This group comprises agents with diverse mechanisms of action, e.g. topoisomerase I and II inhibitors, mitosis inhibitors, and DNA damaging agents. The activity of these are tested in cultured cells using the MTT assay to determine cell number. Cells are treated by addition of drug (at the $GI_{30}$ dose) to the medium, followed twenty-four hours later by addition of GRO29A ($GI_{30}$ dose), pr in the reverse sequence. For combinations for which there is synergistic activity, cells are examined for cell cycle perturbation (by flow cytometry) and apoptosis (flow cytometry of annexin V-stained cells). Synergistic combinations are also tested in vivo, as described above.

Development of Homology Models of Nucleolin and Carrying Out of a "Virtual Screen" of a Library of Small Molecules to Identify Potential Nucleolin Inhibitors. Small molecule inhibitors of nucleolin may be more practical alternatives to oligonucleotides. Homology modeling (with MSI Modeller and Homology programs) is used to build a 3D model of nucleolin from its sequence alignment with known structures of related proteins (16 have been identified). Standard techniques of backbone building, loop modeling, structural overlay and statistical analysis of the resulting models are used. The homology model will be refined using molecular dynamics.

The virtual screen uses the MSI Ludi software combined with the ACD database. Ludi fits molecules into the active site of nucleolin by matching complementary polar and hydrophobic groups. An empirical scoring function is used to prioritize the hits. Ludi also suggests modifications that may increase the binding affinity between the active oligonucleotides and nucleolin, and can also improve the homology model of nucleolin by inference from the binding of the active oligonucleotides. The ACD structural database contains 65,800 commercially and synthetically available chemicals that can be acquired immediately for further development. A selection of the most promising compounds is tested for protein binding and antiproliferative activity in cultured cells and in vivo.

Growth Inhibitory Effects of G-rich Oligonucleotides. The effects of four G-rich phosphodiester oligonucleotides (GROs) on the growth of tumor cells in culture were tested. These oligonucleotides consisted entirely of deoxyguanosine and thymidine and contained at least two contiguous guanosines. For increased stability to serum nucleases, oligonucleotides were modified at the 3'-terminus with a propylamino group. This modification protects the oligonucleotides from degradation in serum containing medium for at least twenty-four hours.

FIGS. 1A-D shows the results of MTT assays for determining relative numbers of viable cells in treated cell lines derived from prostate (DU145), breast (MDA-MB-231, MCF-7) or cervical (HeLa) carcinomas.

Two oligonucleotides, GRO29A and GRO15A, consistently inhibited proliferation in all of the cell lines tested. For three of the cell lines, GRO29A had a more potent inhibitory effect than GRO15A (for MCF-7 cells, the oligonucleotides had similar effects). The growth of cells treated with two other oligonucleotides, GRO15B and GRO26A, was similar to that of the control water-treated cells (GRO26A had a weak growth inhibitory effect in MDA-MB-231 and HeLa cells).

Figure 2A:
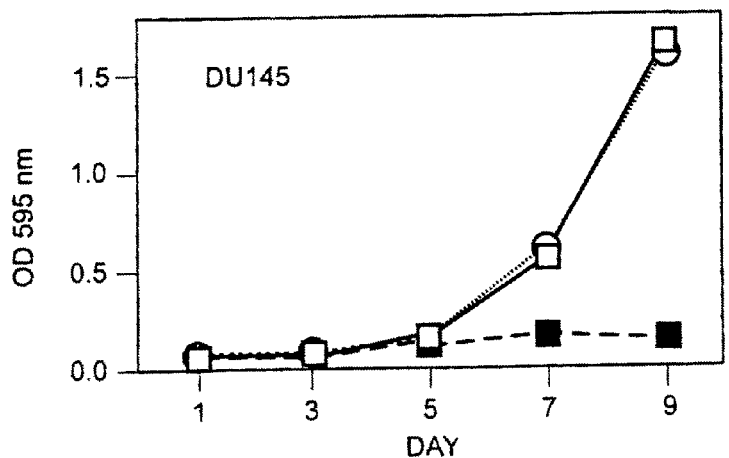
FIG. 2 illustrates the results of MTT assays showing the growth of (A) DU145 cells, (B) MDA-MB-231 cells, and (C) HS27 cells treated with GRO29A active oligonucleotide (closed squares), GRO15B (inactive oligonucleotide, half-filled squares), or no oligonucleotide (open squares).
Figure 2B:
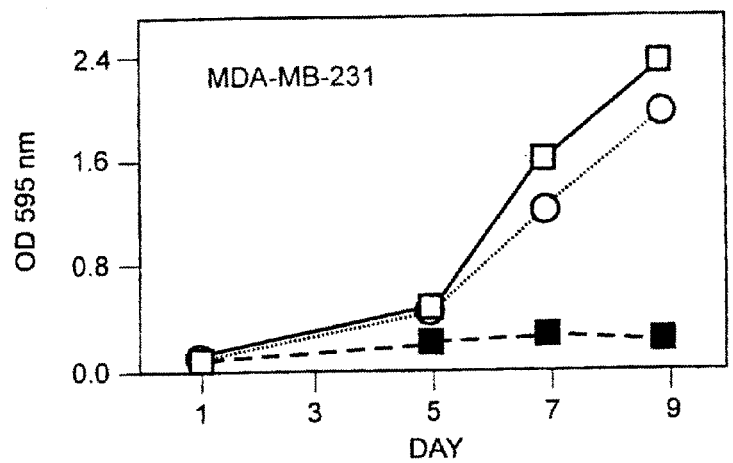
Figure 2C:
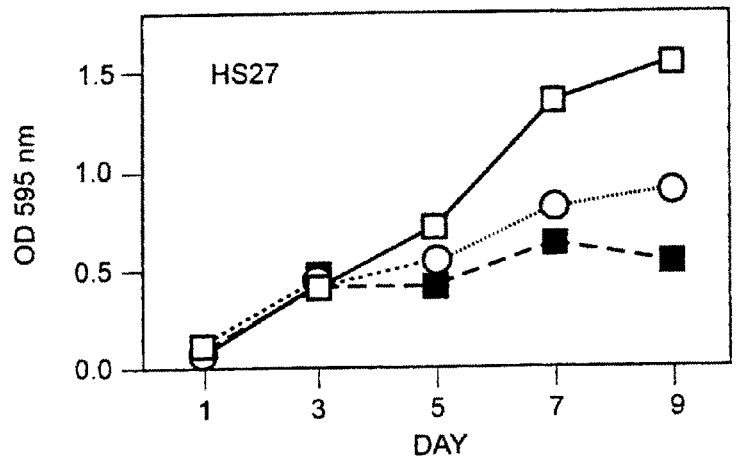

The results illustrated in FIGS. 2A-C show that GRO29A has a lesser growth inhibitory effect on a non-malignant cell line (HS27) compared to most malignant cell lines, for example, DU145, MDA-MG-231. Also, GRO29A has antiproliferative effects against leukemia cell lines, for example, K562 and U937, as shown in FIG. 3. It has a lesser growth inhibitory effect against a non-malignant hematopoictic stem cell line (ATCC 2037).

Figure 4A:
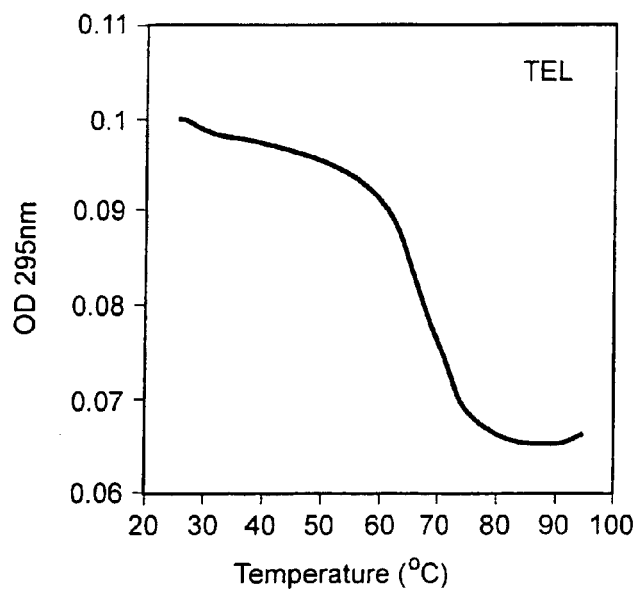
FIG. 4 are U.V. thermal renaturation curves to assess G-quartet formation by G-rich oligonucleotides wherein (A) TEL, (B) GRO29A, (C) GRO15A, (D) GRO15G, and (E) GRO26A.
Figure 4B:
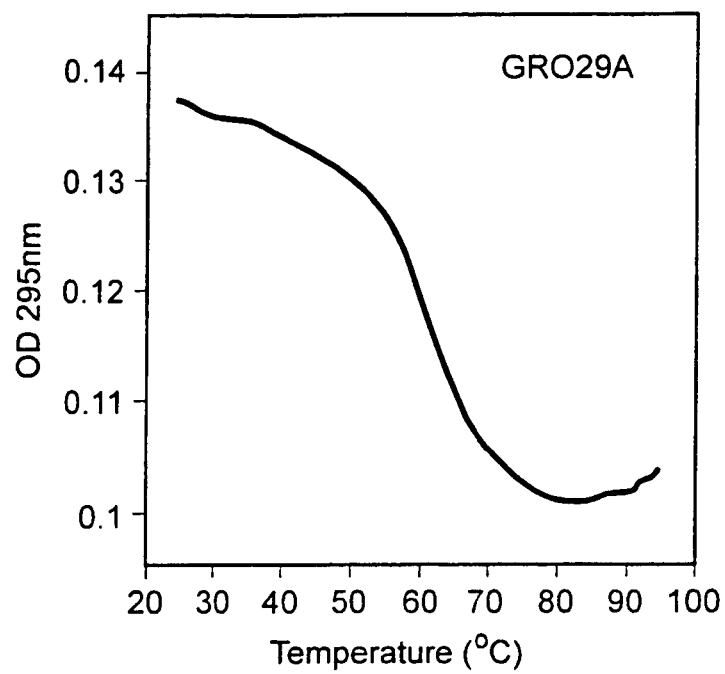
Figure 4C:
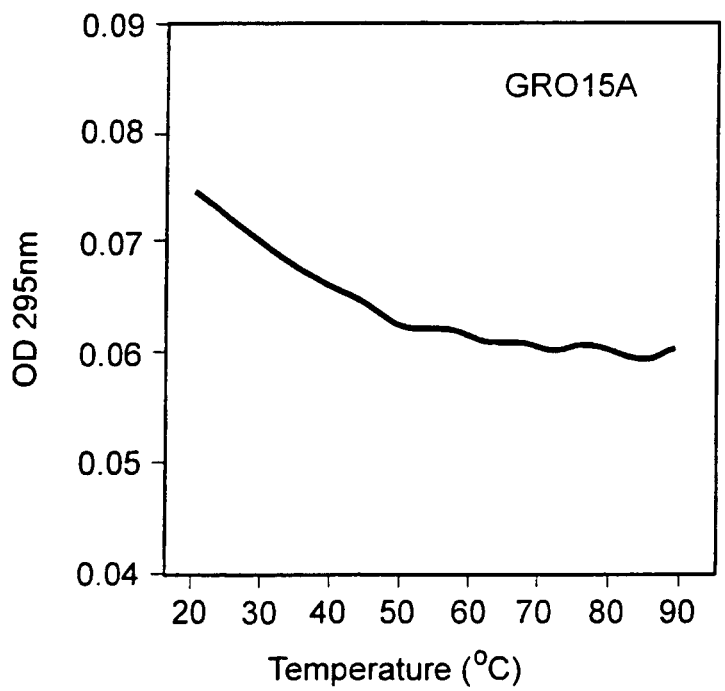
Figure 4D:
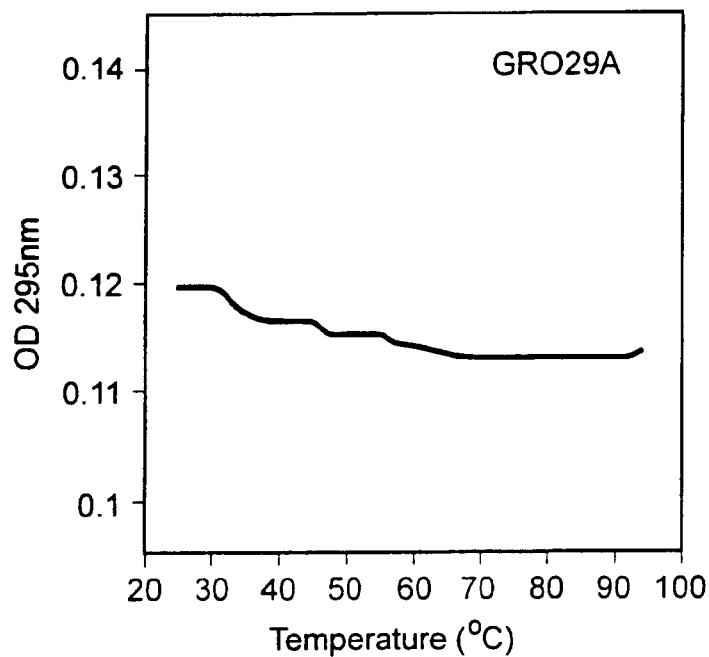
Figure 4E:
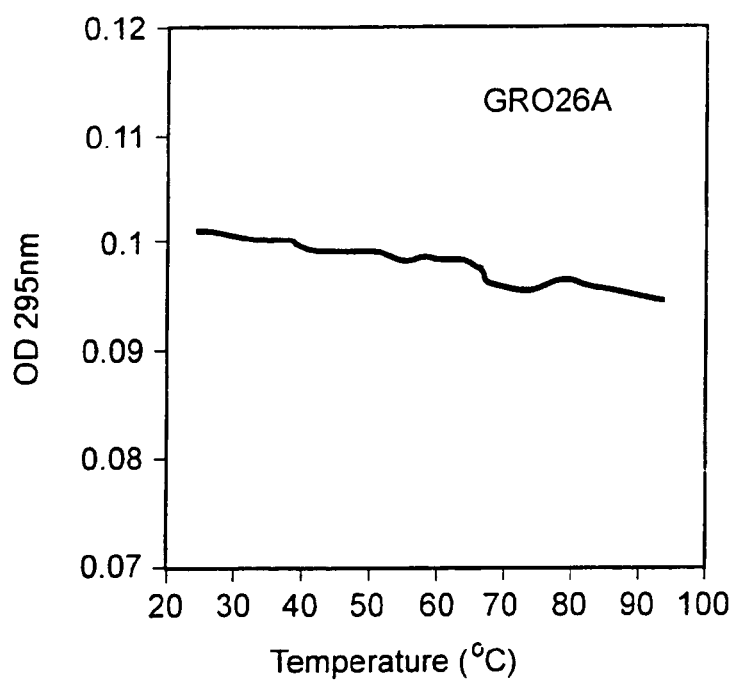

G-quartet Formation by G-rich Oligonucleotides. To investigate the formation of G-quartet structures by the G-rich oligonucleotides, a U.V. melting technique described by Mergny et al. (1998) *FEBS Lett.* 435, 74-78 was used. This method relies on the fact that dissociation of G-quartets leads to a decrease in absorbance at 295 nm and is reported to give a more reliable indication of intramolecular G-quartet formation than measurement at 260 nm n. As a control for G-quartet formation, we used a single-stranded oligonucleotide, TEL. This oligonucleotide contains four repeats of the human telomere sequence 5'-TTAGGG and is known to form a G-quartet structure in vitro. Wang et al. (1993) *Structure* 1, 263-282. FIG. 4A shows the annealing curve for this sequence. G-quartet formation is indicated by a clear transition with a melting temperature of 66° C. The transition was reversible and a slight hysteresis was observed between heating and cooling curves (not shown) at 0.5° C./min indicating a fairly slow transition. The most active oligonucleotide, GRO29A (FIG. 4B), showed a similar profile, clearly indicating the presence of G-quartets. The slightly less active oligonucleotide, GRO15A (FIG. 4C), showed a decrease in absorbance between 20 and 50° C. This is suggestive of G-quartet formation, but a clear transition is not seen since the melting temperature is lower than for TEL (FIG. 4A) or GRO15A (FIG. 4C). The curves for the two inactive oligonucleotides, GRO15B (FIG. 4B) and GRO26A (FIG. 4E), showed no transitions characteristic of intramolecular G-quartet formation under these conditions.

Figure 5:
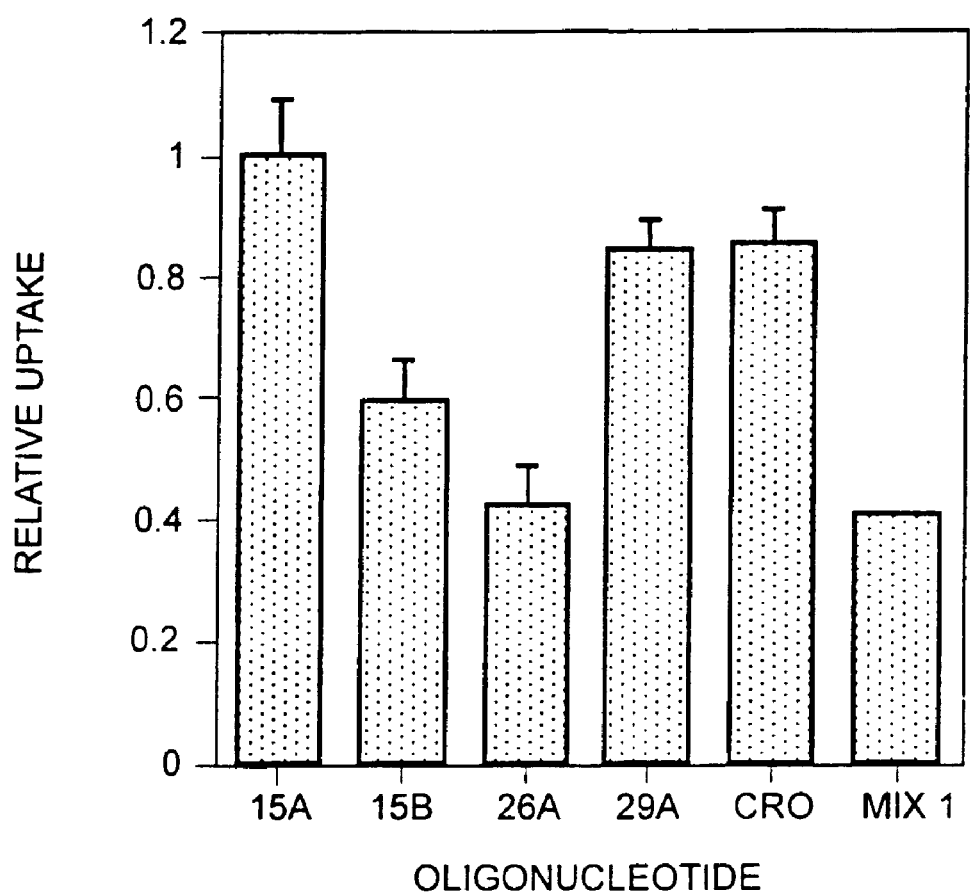
FIG. 5 is a chromatogram illustrating uptake of G-rich oligonucleotide by MDA-MB-231 breast cancer cells.

Relative Uptake of Oligonucleotides. To determine if the antiproliferative activity of G-rich oligonucleotides could be explained by their differential uptake into cells, the cellular uptake of 5'-radiolabeled oligonucleotides was assessed. Although this method may underestimate absolute cellular uptake of oligonucleotide due to the action of phosphomonoesterase in removing the 5'-label, it can provide useful information when comparing relative uptake. Scaggiante et al. (1998) *Eur. J. Biochem.* 252, 207-215; Capaccioli et al. (1993) *Biochem. Biophys. Res. Commun.* 197, 818-825. FIG. 5 shows the relative uptake of oligonucleotides into cells after ten hours, as measured by cell-associated radioactivity. The order of uptake (i.e. GRO15A>GRO29A~CRO>GRO15B>GRO26A>MIX1) was the same at twenty-six hours. The presence of intact oligonucleotide inside cells was verified by polyacrylamide electrophoresis of cell lysates.

Although FIG. 5 shows that there were differences in the extent of oligonucleotide uptake depending on sequence, these did not correlate with antiproliferative activity. For example, an inactive oligonucleotide, CRO (See FIG. 6C), was taken up with similar efficiency to the most active oligonucleotide, GRO29A. Hence, the differential growth inhibitory properties of the oligonucleotides cannot be explained in terms of differences in cell uptake. It was noted that relative uptake appeared to correlate well with the proportion (but not the number) of thymidines in the sequence, but the significance of this observation is not clear at present.

Active G-rich Oligonucleotides Bind to a Specific Cellular Protein. To investigate further the mechanism of the growth inhibitory effects, binding of the oligonucleotides to cellular proteins was examined. 5'-Radiolabeled oligonucleotides were incubated with HeLa nuclear extracts, alone or in the presence of unlabeled competitor oligonucleotide, and examined by an electrophoretic mobility shift assay. The G-quartet forming telomere sequence oligonucleotide, TEL, was included as a competitor in this experiment. A single stranded oligonucleotide, TEL, was also included as a competitor in this experiment. TEL contains four repeats of the human telomere sequence 5'-TTAGGG-3', and is known to form a G-quartet structure in vitro. Wang et al. (1993) *Structure* 1, 263-282. FIG. 6A shows the formation of a stable protein-oligonucleotide complex (marked "*"). This band was intense when the labeled oligonucleotide was one of the growth inhibitory oligonucleotides, GRO15A or GRO29A (lanes 1 and 5), but the inactive oligonucleotide, GRO26A, formed only a weak complex (lane 9). This experiment also showed that the complex could be effectively competed by either unlabeled antiproliferative oligonucleotide or TEL, but not by the inactive GRO26A.

To further confirm that the same protein is binding to TEL and to the growth inhibitory oligonucleotides, a similar experiment was carried out in which TEL was labeled. Labeled TEL formed two complexes with nuclear extracts in the absence of competitor oligonucleotides (bands A and B, FIG. 6B). The slower migrating TEL-protein complex (band A) was competed for by unlabeled growth inhibitory oligonucleotides (GRO15A, GRO29A) but not inactive oligonucleotides (GRO26A, GRO15B). The faster migrating complex (band B) was specific for TEL and was not competed for by G-rich oligonucleotides. Hence binding of competitor GROs was characterized by a decrease in the intensity of band A and an increase in the intensity of band B (due to release of labeled TEL from band A complex). This assay allowed comparison of the binding affinity of native GROs (without 5'-phosphorylation) and was used for assessment of protein binding in subsequent experiments. To ensure that competition was due to binding of the GRO to the protein component of complex A, and not a result of interaction between GRO and TEL oligonucleotide, a mobility shift on a 15% polyacrylamide gel was carried out. No shifted bands were observed when labeled TEL was incubated with GROs in the absence of protein (data not shown).

Figure 6C:
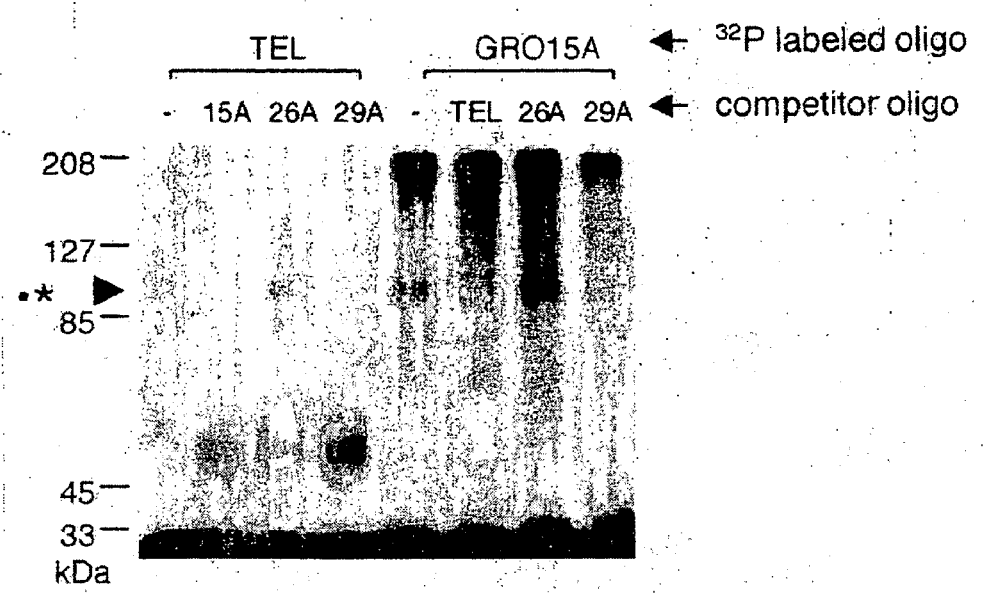

To determine the approximate molecular weight of the protein involved in complex A, and to confirm that competition for this complex results from direct binding of the protein to oligonucleotides, a U.V. cross-linking study was carried out. 5'-Labeled oligonucleotides and HeLa nuclear extracts were incubated alone or in the presence of unlabeled competitor oligonucleotides. The samples were then irradiated with U.V. light resulting in cross-link formation between protein residues and thymidines in the oligonucleotide. The protein was thus radiolabeled and could be detected on a SDS-polyacrylamide gel. FIG. 6C shows the results of this experiment. Both TEL and GRO15A crosslinked to a protein (marked "*") which was competed for by antiproliferative oligonucleotides and TEL, but not by inactive GRO26A. The most active oligonucleotide, GRO29A, also formed this approximately 100 kDa complex and another complex of higher molecular weight (not shown). Inactive GRO26A produced a barely visible band at approximately 100 kDa (not shown).

Figure 6D:
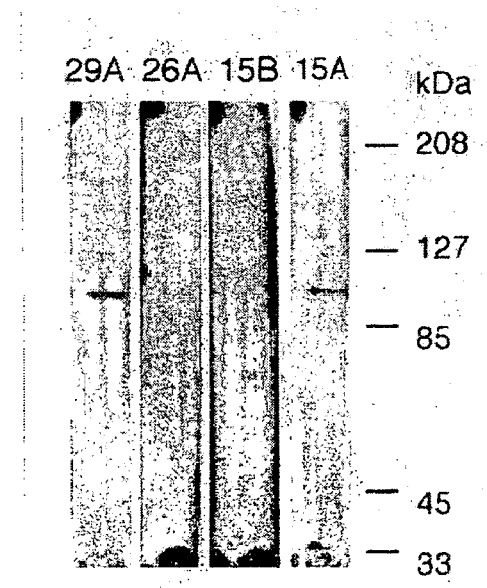

The molecular weight of the nuclear protein was more accurately determined by Southwestern blotting. HeLa nuclear extracts were electrophoresed on an 8% polyacrylamide-SDS gel and transferred to a PVDF membrane. The membrane was blocked and cut into strips. Each strip was incubated at 4° C. with a $^{32}$P-labeled G-rich oligonucleotide in the presence of unrelated unlabeled double stranded and single stranded DNA to block non-specific binding. FIG. 6D shows active oligonucleotides GRO15A and GRO29A hybridized to a single protein band at 106 kDa (the band was exactly adjacent to a 106 kDa molecular mass marker, not shown). Inactive oligonucleotides GRO15B and GRO26A hybridized only weakly to this protein. The data presented in FIG. 6 suggest a correlation between activity and protein binding, at least for the four oligonucleotides examined. These experiments also demonstrate that binding of GROs to p106 is highly specific, since only a single protein band is recognized with high affinity (see FIG. 6D). This was not simply a result of hybridization to an abundant protein, as India ink staining of immobilized nuclear extracts showed the presence of many other protein bands which were equally or more intense than the band at 106 kDa (data not shown).

Figure 7C:
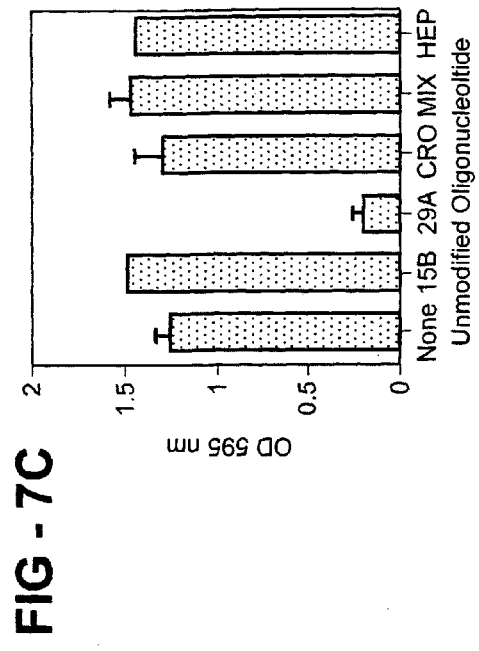
FIG. 7: (A) is a chromatogram illustrating an MTT assay of MDA-MB-231 cells treated with a single 10 µM dose of G-rich oligonucleotide or PBS as a control, the assay was performed on day 9 (oligonucleotide added on day 1); (B) illustrates an EMSA showing complex formed by binding of 5 µg of MDA-MB-231 nuclear extracts to $^{32}$P-labeled TEL oligonucleotide and competition by unlabeled G-rich oligonucleotides (10-fold molar excess); (C) is a chromatogram illustrating the results of a MTT assay of MDA-MB-231 cells treated with a single 10 µM dose of 3'-protected C-rich oligonucleotide (CRO) or mixed sequence oligonucleotide (MIX1) or with 20 units/ml heparin (HEP), in comparison with inactive (GRO15B) and active (GRO29A) G-rich oligonucleotides wherein the assay was performed on day 7; and (D) is a chromatogram illustrating the results of an MTT assay of MDA-MB-231 cells treated with a single 10 µM dose of unmodified mixed sequence oligonucleotides, in comparison with an unmodified GRO29A analog (29A-OH) and TEL wherein to treat the cells, the culture medium was replaced by serum-free medium containing 10 µM oligonucleotide and after four hours at 37° C., fetal calf serum was added to give 10% v/v and the assay was performed on day 7.
Figure 7D:
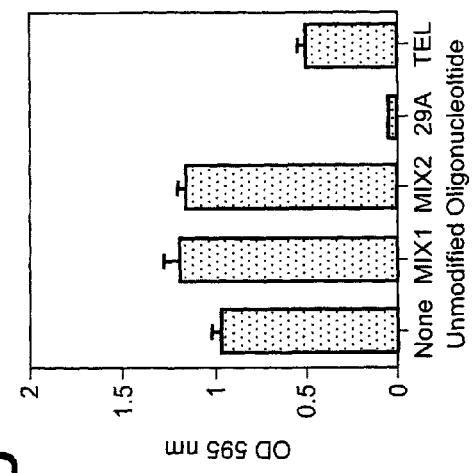
Figure 7A:
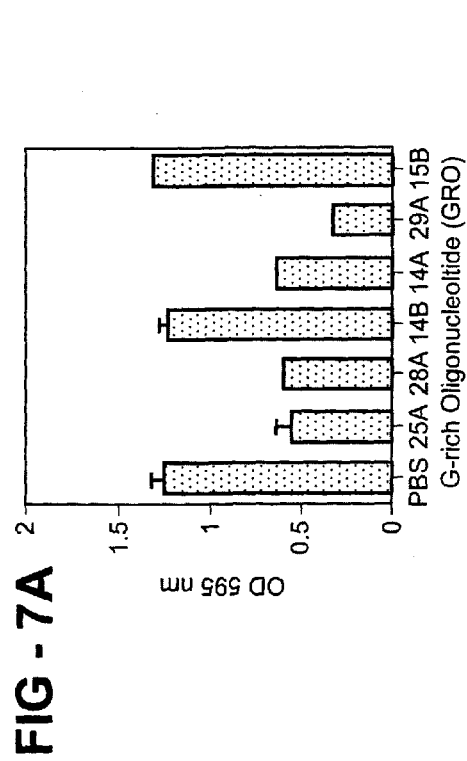
Figure 7B:
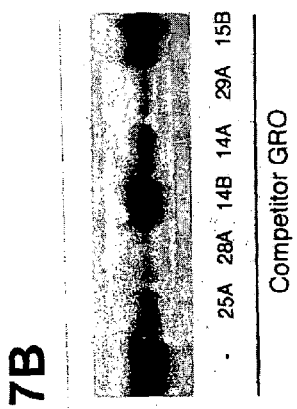

Antiproliferative Activity Correlates with Protein Binding. To further confirm the relationship between activity and binding to the 106 kDa protein, four more G-rich oligonucleotides were synthesized and their effects were compared with active (GRO29A) and inactive (GRO15B) oligonucleotides. FIGS. 7A and 7B show that the growth inhibitory effect of the oligonucleotides correlated with their ability to compete for the TEL-binding protein. Three of the new oligonucleotides (GRO14A, GRO25A, GRO28A) displayed a moderate antiproliferative activity but were not as potent as GRO29A. Oligonucleotide GRO14B showed no antiproliferative activity. Correspondingly, the moderate active oligonucleotides were able to compete with TEL for binding to the nuclear protein, though not as effectively as GRO29A. The non-inhibitory oligonucleotide, GRO14B, was unable to compete for protein binding.

Figure 8:
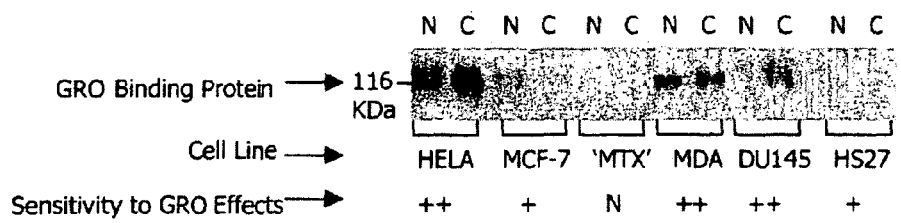
FIG. 8: (Top) Southwestern blot using radiolabeled GRO15A to detect GRO binding protein in nuclear (N) and cytoplasmic (C) extracts from various cell lines. (Bottom): Sensitivity of various cell lines to the growth inhibitory effects of GRO29A and GRO15A.
Figure 11:
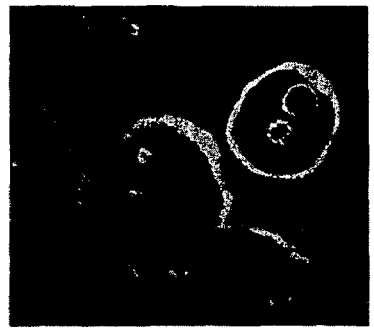
FIG. 11: Staining of non-permeabilized DU145 cells with nucleolin antibody, showing the presence of nucleolin in the plasma membrane.

The importance of the approximately 106 kDa protein in GRO effects was further demonstrated by the correlation between the sensitivity of various cell lines to the GRO-induced antiproliferative effects and levels of this protein in nuclear and cytoplasmic extracts from these cell lines, as shown in FIG. 8.

Effects of Non-G-rich Oligonucleotides. To investigate the specificity of the antiproliferative effects, the growth inhibitory effects of non-G-rich oligonucleotides and heparin, a polyanionic polysaccharide, were examined. FIG. 7C shows that at 10 µM concentration (equivalent to approximately 0.1 mg/ml for GRO29A), neither a 3'-modified C-rich oligonucleotide (CRO) nor a 3'-modified mixed base oligonucleotide (MIX1) were able to inhibit the growth of MDA-MB-231 breast cancer cells. This result showed that the growth inhibiting activity of GRO15A and GRO29A was not simply nonspecific effects resulting from the presence of 3'-modified oligonucleotide but rather relied on some unique feature of these sequences. Heparin also had no effect on cell growth when added to the culture medium at a concentration of 20 units/ml (approximately 0.12 mg/ml), further demonstrating that the antiproliferative effects of active oligonucleotides are not simply a result of their polyanionic character. To examine the antiproliferative properties of non-3'-protected oligonucleotides, a slightly modified treatment protocol was used in which oligonucleotides were added to cells in serum-free medium (see "Experimental Procedures"). FIG. 7D shows that similar effects could also be seen with unmodified oligonucleotides under these conditions. Both 29A-OH (a 3'-unmodified analog of GRO29A) and TEL inhibited the growth of cells, whereas two mixed sequence oligonucleotides had no growth inhibitory effects.

The protein binding properties of these non-G-rich oligonucleotides and heparin (not shown) were also compared. As expected, the unlabeled growth inhibitory oligonucleotides GRO29A, 29A-OH, and TEL competed strongly for protein binding in the competitive electrophoretic mobility shift assay (using labeled TEL oligonucleotide and MDA-MB-231 nuclear extracts) at 10 nM concentration (approximately 0.1 µg/ml for GRO29A). In accord with its lesser antiproliferative activity, TEL competed slightly less effectively than 29A-OH or GRO29A. No competition was observed using 10 nM unlabeled CRO, MIX2, or MIX3 or in the presence of 0.02 units/ml heparin (approximately 0.12 µg/ml). However, the mixed sequence oligonucleotide, MIX1, was anomalous. Although this oligonucleotide had no effect on the growth of cells, it appeared to compete for protein binding in the competitive EMSA.

Figure 9A:
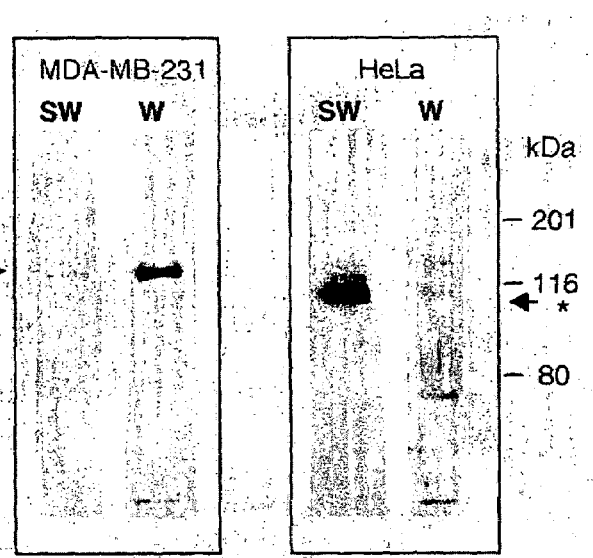
FIG. 9: (A) Southwestern (SW) and Western (W) blots probed respectively with $^{32}$P-labeled active G-rich oligonucleotide (GRO15A) or nucleolin antiserum. Left panel shows MDA-MB-231 nuclear extracts (5 µg/lane); right panel shows HeLa nuclear extracts (Promega Inc., 5 µg/lane). (B) Southwestern and Western blots of proteins captured from the lysates of MDA-MB-231 cells which had been treated with no oligonucleotide (none), active G-rich oligonucleotide (15A) or less active G-rich oligonucleotide (15B). (C) Southwestern and Western blots showing binding of GRO15A and nucleolin antibody to protein extracts (3 µg/lane) from MDA-MB-231 cells: nuclear extracts (NU), cytoplasmic extracts (CY) and membrane proteins (ME).

Evidence that G-rich Oligonucleotide Binding Protein is Nucleolin. Two previous reports describe binding of the nucleolar protein, nucleolin, to the G-rich telomere sequence. Ishikawa et al. ((1993) *Mol. Cell. Biol.* 13, 4301-4310) identified a 50 kDa protein from HeLa extracts which bound to 5'-(TTAGGG)$_4$-3'. Microsequence determination suggested that this was a proteolytic fragment of nucleolin. Binding of the full-length, purified 106 kDa nucleolin protein was demonstrated independently by Dickinson and Kohwi-Shigematsu. Dickinson et al. (1995) *Mol. Cell. Biol.* 15, 456-465. Since the subject protein was of the correct molecular weight and also bound to 5'-(TTAGGG)$_4$-3' (TEL), the hypothesis that the G-rich oligonucleotide binding protein was nucleolin was tested. Nuclear extracts from HeLa cells (purchased from Promega) or MDA-MG-231 breast cancer cells (obtained in Applicants laboratory by standard procedures) were electrophoresed and transferred to PVDF membrane. The immobilized proteins were probed for binding to $^{32}$P labeled GRO15A using the Southwestern procedure described, and visualized by overnight exposure to autoradiographic film. The same membrane was stripped of oligonucleotide by the denaturation/renaturation steps described (Experimental Procedures, see "Southwestern Blotting") and Western-blotted using nucleolin antiserum as primary antibody and a horseradish peroxidase (HRP) conjugated anti-rabbit secondary antibody. The blot was visualized by incubation with a chemiluminescence detection reagent followed by a twenty second exposure to autoradiographic film. The results are shown in FIG. 9A. Southwestern blots of nuclear extracts showed an intense band upon hybridization and radiolabeled GRO15A, at 106 kDa (HeLa) or approximately 116 kDa (MDA-MB-231). The Western blot of MDA-MB-231 nuclear proteins shows one intense band at approximately 116 kDa and weaker bands at about 50 kDa. In HeLa extracts the nucleolin antibody recognizes multiple bands at approximately 50, 75, 106 and 120 kDa. Most importantly, in both cell lines the band that was recognized by GRO15A exactly corresponded to a band recognized when the membrane was stripped and Western blotted with nucleolin antibody. Nucleolin is a protein that can be phosphorylated in cells by a number of kinases, and is also susceptible to self-proteolysis. Zhou et al. (1997) *J. Biol. Chem.* 272, 31130-31137; Schwab et al. (1997) *Eur. J. Cell Biol.* 73, 287-297; Li et al. (1996) *J. Biol. Chem.* 271, 15662-15668; Peter et al. (1990) *Cell* 60, 791-801; Belenguer et al. (1990) *Mol. Cell. Biol.* 10, 3607-3618; Fang et al. (1993) *Exp. Cell Res.* 208, 48-53; Chen et al. (1991) *J. Biol. Chem.* 266, 7754-7758. It is believed that the difference in the molecular weights of proteins detected in these blots may arise from the different methods of preparation of the nuclear extract leading to differently phosphorylated or degraded forms of nucleolin being the predominant species. The difference in the intensities of the bands shown in the Southwestern blots in FIG. 9A may be due to the preferential binding of GRO15A to one form of nucleolin (apparently the 106 kDa species) over others.

Figure 9B:
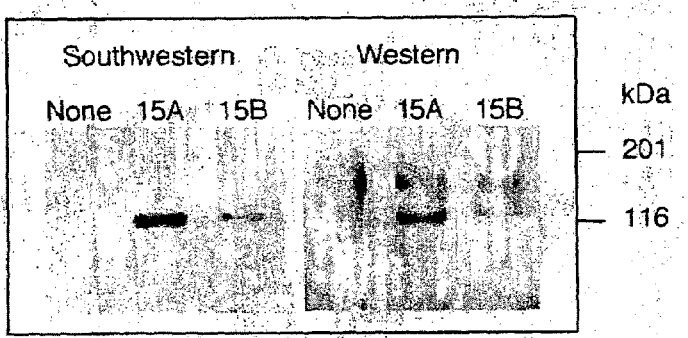

To determine whether binding of the specific protein occurred within the cell environment, biotinylated G-rich oligonucleotides were used to treat MDA-MB-231 breast cancer cells. Streptavidin-coated magnetic beads were then used to capture oligonucleotide-protein complexes after lysing the cells with an immunoprecipitation-type buffer (see "Experimental Procedures"). This procedure was carried out for cells that were treated with either an active oligonucleotide (5'-Biotin-GRO15A) or an inactive oligonucleotide (5'-Biotin-GRO15B), and untreated cells as a control. Equal volumes of each sample were electrophoresed and transferred to a PVDF membrane. This was analyzed by India ink staining, Southwestern blotting with radiolabeled GRO15A, and Western blotting with a nucleolin monoclonal antibody. India ink staining of the membrane showed a major protein band at approximately 116 kDa which was present in cells treated with biotinylated GRO15A, but was absent in untreated cells and of a much lower intensity in cells treated with inactive biotinylated GRO15B (data not shown). The Southwestern and Western blots (FIG. 9B) confirm that this captured protein binds to both GRO 15A and a nucleolin antibody.

This experiment showed that a 116 kDa protein was specifically captured from cells treated with biotinylated GROs, that this protein was recognized also by a nucleolin antibody, and also, that more of this protein was captured by active GRO15A than was captured by the less active GRO15B. Although the possibility that the protein-oligonucleotide association took place during cell lysis or oligonucleotide capture cannot be absolutely excluded, it is unlikely that the oligonucleotide would exist in a free, uncomplexed state inside the cell. These results provide strong evidence for binding of oligonucleotide to the 116 kDa protein inside the cell (or possibly at the cell surface).

Figure 9C:
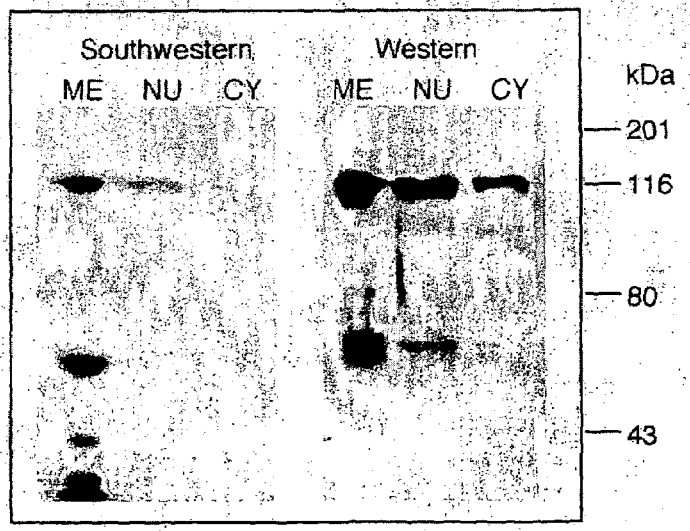
Figure 12C:
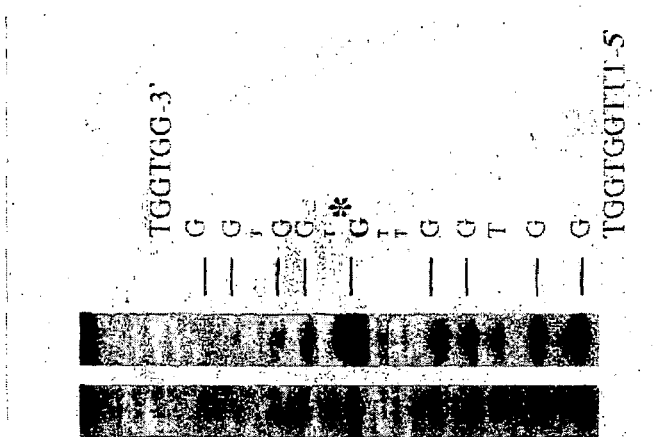
FIG. 12: (A) G-quartet, illustrating hydrogen bonding interaction. (B) Molecular model of GRO29A, showing a proposed dimeric structure stabilized by 8 G-quartets. (C) Dimethyl sulfate footprinting of GRO29A, showing preferential methylation of the loop region guanosine, consistent with the predicted model.
Figure 12B:
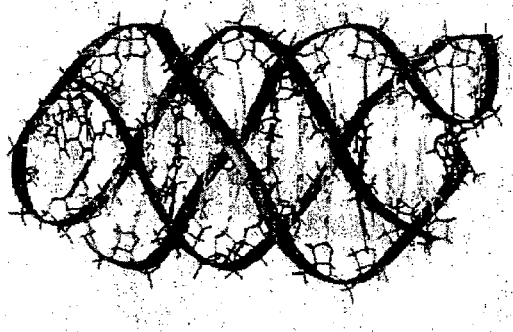
Figure 12A:
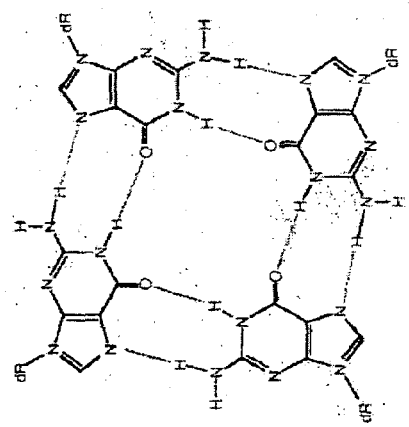
Figures 13A, 13B:
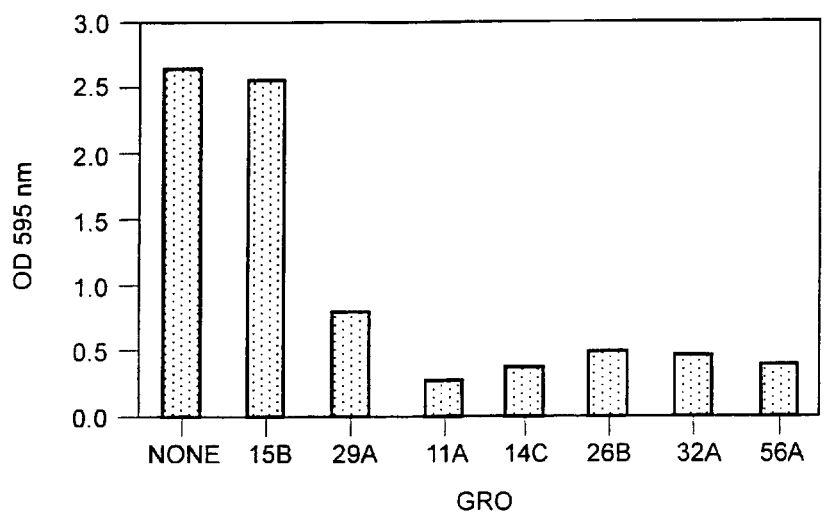
FIG. 13: (A) MTT assay showing antiproliferative activity of novel guanosine-rich oligonucleotides against MDA-MB-231 breast cancer cells. (B) Sequences of novel guanosine-rich oligonucleotides.

To determine the subcellular location of the G-rich oligonucleotide binding protein Southwestern and Western blotting experiments were carried out to compare nuclear extracts, cytoplasmic extracts and proteins derived from the cell membrane (5 µg of extract per lane). FIG. 9C shows the results of these studies. The Southwestern blot shows a 116 kDa protein capable of binding labeled GRO15A is present in the nuclear extracts and, to a lesser extent, in the cytoplasmic fraction. The same band was present in plasma membrane extracts and hybridized strongly to GRO15A. Western blotting of the same membrane showed that a monoclonal antibody to nucleolin also recognized these bands at 116 kDa in each fraction. (A band at approximately 70 kDa was also recognized by both GRO15A and nucleolin antibody and may be a proteolytic fragment of nucleolin.) Since both the location and relative intensity of the bands recognized by GRO15A and nucleolin antibody are the same, these results provide further evidence that the protein that binds to antiproliferative G-rich oligonucleotides is nucleolin. The detection of GRO binding protein in the plasma membrane extracts also suggests the possibility that binding to cell surface protein may be important in the mechanism of action of G-rich oligonucleotides.

Furthermore, the involvement of nucleolin/GRO-binding protein in the antiproliferative activity of GRO was shown as the sensitivity of cell lines to GRO effects was found to be related to levels of GRO binding protein (detected by Southwestern blotting of cell extracts). For example, cell lines which are most sensitive to GRO effects (DE145, MDA-MB-231, HeLa) had high levels of p110, whereas less sensitive cell lines (HS27, MCF-7) or resistant cell lines (a methotrexate-resistant MCF-7 derivative) had low or undetectable levels of p 110. Additionally, nucleolin levels were found to be significantly altered by GRO-treated cells and untreated cells in exponential growth as shown in FIG. 9 wherein an overall increase in immunofluorescence was found for treated (B) vs. untreated (A) MDA-MB-231 cells seventy-two hours following GRO29A treatment using anti-nucleolin staining and a translocation to the cytoplasm was also observed.

The TEL-protein complex is competed for most effectively by GRO29A and OMR29A (lanes 2 and 13), which are two potent antiproliferative oligonucleotides. The complex is not competed for, or is competed to a lesser extent, by compounds with no antiproliferative activity (e.g. caffeine, polymyxin or heparin) or by commonly used therapeutic agents whose mechanisms are known to result from properties other than nucleolin binding (e.g. 5-FU, taxol or cis-platin).

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition comprising an isolated oligonucleotide consisting of SEQ ID NO: 5, 6, 10, 12 or 17.

2. The composition of claim 1, wherein the oligonucleotide is capable of forming a guanosine-quartet structure.

3. The composition of claim 1, wherein the oligonucleotide has a 3' end and a 5' end, and wherein the 3' end is modified to alter a property of the nucleolin binding oligonucleotide.

4. The composition of claim 3, wherein the 3' end of the oligonucleotide comprises a propylamine group.

5. The composition of claim 1, wherein the oligonucleotide comprises a DNA, RNA, 2'-O-methyl or phosphorothioate backbone.

6. The composition of claim 1, wherein the oligonucleotide is capable of inhibiting nucleolin activity, thereby inhibiting cell proliferation.

7. The composition of claim 6, wherein the cell proliferation is neoplastic or dysplastic growth.

8. The composition of claim 6, wherein the cell proliferation is that of breast cancer, prostate cancer, cervical cancer, lung cancer, or tumor cells.

* * * * *

SEQUENCE LISTING

```
<160> NUMBER OF SEQ ID NOS: 21

<210> SEQ ID NO 1
<211> LENGTH: 14
<212> TYPE: DNA
<213> ORGANISM: Artificial Sequence
<220> FEATURE:
<223> OTHER INFORMATION: GRO14A

<400> SEQUENCE: 1
gttgtttggg gtgg                                                         14

<210> SEQ ID NO 2
<211> LENGTH: 15
<212> TYPE: DNA
<213> ORGANISM: Artificial Sequence
<220> FEATURE:
<223> OTHER INFORMATION: GRO15A

<400> SEQUENCE: 2
gttgtttggg gtggt                                                        15

<210> SEQ ID NO 3
<211> LENGTH: 25
<212> TYPE: DNA
<213> ORGANISM: Artificial Sequence
<220> FEATURE:
<223> OTHER INFORMATION: GRO25A

<400> SEQUENCE: 3
ggttggggtg ggtggggtgg gtggg                                             25

<210> SEQ ID NO 4
<211> LENGTH: 28
<212> TYPE: DNA
<213> ORGANISM: Artificial Sequence
<220> FEATURE:
<223> OTHER INFORMATION: GRO28A

<400> SEQUENCE: 4
tttggtggtg gtggttgtgg tggtggtg                                          28
```

```
<210> SEQ ID NO 5
<211> LENGTH: 29
<212> TYPE: DNA
<213> ORGANISM: Artificial Sequence
<220> FEATURE:
<223> OTHER INFORMATION: GR029A

<400> SEQUENCE: 5
tttggtggtg gtggttgtgg tggtggtgg                                          29

<210> SEQ ID NO 6
<211> LENGTH: 29
<212> TYPE: DNA
<213> ORGANISM: Artificial Sequence
<220> FEATURE:
<223> OTHER INFORMATION: GR029-2

<400> SEQUENCE: 6
tttggtggtg gtggttttgg tggtggtgg                                          29

<210> SEQ ID NO 7
<211> LENGTH: 29
<212> TYPE: DNA
<213> ORGANISM: Artificial Sequence
<220> FEATURE:
<223> OTHER INFORMATION: GR029-3

<400> SEQUENCE: 7
tttggtggtg gtggtggtgg tggtggtgg                                          29

<210> SEQ ID NO 8
<211> LENGTH: 29
<212> TYPE: DNA
<213> ORGANISM: Artificial Sequence
<220> FEATURE:
<223> OTHER INFORMATION: GR029-5

<400> SEQUENCE: 8
tttggtggtg gtggtttggg tggtggtgg                                          29

<210> SEQ ID NO 9
<211> LENGTH: 13
<212> TYPE: DNA
<213> ORGANISM: Artificial Sequence
<220> FEATURE:
<223> OTHER INFORMATION: GR029-13

<400> SEQUENCE: 9
tggtggtggt ggt                                                           13

<210> SEQ ID NO 10
<211> LENGTH: 11
<212> TYPE: DNA
<213> ORGANISM: Artificial Sequence
<220> FEATURE:
<223> OTHER INFORMATION: GR011A

<400> SEQUENCE: 10
ggtggtggtg g                                                             11

<210> SEQ ID NO 11
<211> LENGTH: 14
<212> TYPE: DNA
<213> ORGANISM: Artificial Sequence
<220> FEATURE:
<223> OTHER INFORMATION: GR014C
```

```
<400> SEQUENCE: 11
ggtggttgtg gtgg                                                        14

<210> SEQ ID NO 12
<211> LENGTH: 26
<212> TYPE: DNA
<213> ORGANISM: Artificial Sequence
<220> FEATURE:
<223> OTHER INFORMATION: GR026B

<400> SEQUENCE: 12
ggtggtggtg gttgtggtgg tggtgg                                           26

<210> SEQ ID NO 13
<211> LENGTH: 56
<212> TYPE: DNA
<213> ORGANISM: Artificial Sequence
<220> FEATURE:
<223> OTHER INFORMATION: GR056A

<400> SEQUENCE: 13
ggtggtggtg gttgtggtgg tggtggttgt ggtggtggtg gttgtggtgg tggtgg          56

<210> SEQ ID NO 14
<211> LENGTH: 32
<212> TYPE: DNA
<213> ORGANISM: Artificial Sequence
<220> FEATURE:
<223> OTHER INFORMATION: GR032A

<400> SEQUENCE: 14
ggtggttgtg gtggttgtgg tggttgtggt gg                                    32

<210> SEQ ID NO 15
<211> LENGTH: 32
<212> TYPE: DNA
<213> ORGANISM: Artificial Sequence
<220> FEATURE:
<223> OTHER INFORMATION: GR032B

<400> SEQUENCE: 15
tttggtggtg gtggttgtgg tggtggtggt tt                                    32

<210> SEQ ID NO 16
<211> LENGTH: 29
<212> TYPE: DNA
<213> ORGANISM: Artificial Sequence
<220> FEATURE:
<223> OTHER INFORMATION: GR029-6

<400> SEQUENCE: 16
ggtggtggtg gttgtggtgg tggtggttt                                        29

<210> SEQ ID NO 17
<211> LENGTH: 28
<212> TYPE: DNA
<213> ORGANISM: Artificial Sequence
<220> FEATURE:
<223> OTHER INFORMATION: GR028B

<400> SEQUENCE: 17
tttggtggtg gtggtgtggt ggtggtgg                                         28

<210> SEQ ID NO 18
```

```
<211> LENGTH: 10
<212> TYPE: DNA
<213> ORGANISM: Artificial Sequence
<220> FEATURE:
<223> OTHER INFORMATION: GRO13A

<400> SEQUENCE: 18
tggtggtggt                                                          10

<210> SEQ ID NO 19
<211> LENGTH: 35
<212> TYPE: DNA
<213> ORGANISM: Artificial Sequence
<220> FEATURE:
<223> OTHER INFORMATION: mixed sequence 35-mer oligonucleotide

<400> SEQUENCE: 19
tcgagaaaaa ctctcctctc cttccttcct ctcca                              35

<210> SEQ ID NO 20
<211> LENGTH: 24
<212> TYPE: DNA
<213> ORGANISM: Artificial Sequence
<220> FEATURE:
<223> OTHER INFORMATION: 5'- 32P-labeled TEL oligonucleotide

<400> SEQUENCE: 20
ttagggttag ggttagggtt aggg                                          24

<210> SEQ ID NO 21
<211> LENGTH: 26
<212> TYPE: DNA
<213> ORGANISM: Artificial Sequence
<220> FEATURE:
<223> OTHER INFORMATION: control oligonucleotide

<400> SEQUENCE: 21
gactgtaccg aggtgcaagt actcta                                        26
```